(12) United States Patent
Drees et al.

(10) Patent No.: US 9,314,640 B2
(45) Date of Patent: Apr. 19, 2016

(54) TOUCH SCREEN FINGER POSITION INDICATOR FOR A SPINAL CORD STIMULATION PROGRAMMING DEVICE

(71) Applicant: Greatbatch Ltd., Clarence, NY (US)

(72) Inventors: Scott F. Drees, Dallas, TX (US); Norbert F. Kaula, Arvada, CO (US); Yohannes Iyassu, Denver, CO (US); Scott G. Leyh, Cleveland Heights, OH (US); Richard J. Polefko, Parma, NY (US); Stephen C. Trier, Mayfield Heights, OH (US); Raymond L. Yoder, Willoughby, OH (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 14/926,152

(22) Filed: Oct. 29, 2015

(65) Prior Publication Data

US 2016/0045750 A1   Feb. 18, 2016

Related U.S. Application Data

(60) Division of application No. 14/011,156, filed on Aug. 27, 2013, now Pat. No. 9,180,302, which is a continuation-in-part of application No. 13/600,875, filed on Aug. 31, 2012, now Pat. No. 8,903,496.

(60) Provisional application No. 61/695,394, filed on Aug. 31, 2012.

(51) Int. Cl.
*A61N 1/00* (2006.01)
*A61N 1/372* (2006.01)
(Continued)

(52) U.S. Cl.
CPC ............ *A61N 1/37247* (2013.01); *G06F 3/044* (2013.01); *G06F 3/0412* (2013.01);
(Continued)

(58) Field of Classification Search
CPC ........... A61N 1/37247; A61N 1/36021; A61N 1/3605; A61N 1/37252
USPC ..................................................... 607/59, 46
See application file for complete search history.

(56) References Cited

U.S. PATENT DOCUMENTS 3,386,882 A   6/1968   Thomas et al.
4,432,360 A   2/1984   Mumford et al.
(Continued)

FOREIGN PATENT DOCUMENTS

EP   1192972   4/2002
EP   2277586   1/2011
(Continued)

OTHER PUBLICATIONS

"Boston Scientific Precision Spectra System Programming Manual", 2010, 1-580.
(Continued)

*Primary Examiner* — Nicole F Lavert
*Assistant Examiner* — Nadia A Mahmood
(74) *Attorney, Agent, or Firm* — Haynes & Boone, LLP

(57) ABSTRACT

A method of visualizing a user interaction with a clinician programmer is disclosed. A user engagement with respect to a screen of the clinician programmer is detected via one or more sensors associated with the screen of the clinician programmer. One or more locations on the screen of the clinician programmer corresponding to the user engagement is determined. An external monitor is communicatively coupled to the clinician programmer. The external monitor displays one or more cursors that graphically represent the one or more locations on the screen of the clinician programmer corresponding to the user engagement, respectively.

10 Claims, 13 Drawing Sheets

(51) Int. Cl.
- *G06F 3/041* (2006.01)
- *G06F 3/044* (2006.01)
- *G06F 3/0488* (2013.01)
- *G06F 3/0481* (2013.01)
- *G09G 3/36* (2006.01)

(52) U.S. Cl.
CPC ......... *G06F3/0488* (2013.01); *G06F 3/04812* (2013.01); *G09G 3/36* (2013.01); *G06F 2203/04104* (2013.01); *G06F 2203/04801* (2013.01)

(56) References Cited

U.S. PATENT DOCUMENTS

| | | |
|---|---|---|
| 5,286,202 A | 2/1994 | de Gyarfas et al. |
| 5,304,206 A | 4/1994 | Baker et al. |
| 5,312,446 A | 5/1994 | Holschbach et al. |
| 5,370,672 A | 12/1994 | Fowler et al. |
| 5,383,914 A | 1/1995 | O'Phelan |
| 5,421,830 A | 6/1995 | Epstein et al. |
| 5,570,113 A | 10/1996 | Zetts |
| 5,628,776 A | 5/1997 | Paul et al. |
| 5,713,937 A | 2/1998 | Nappholz et al. |
| 5,722,999 A | 3/1998 | Snell |
| 5,724,996 A | 3/1998 | Piunti |
| 5,819,740 A | 10/1998 | Muhlenberg |
| 5,879,374 A | 3/1999 | Powers et al. |
| 5,905,500 A | 5/1999 | Kamen et al. |
| 5,938,690 A | 8/1999 | Law et al. |
| 6,016,447 A | 1/2000 | Juran et al. |
| 6,016,448 A | 1/2000 | Busacker et al. |
| 6,052,624 A | 4/2000 | Mann |
| 6,083,156 A | 7/2000 | Lisiecki |
| 6,148,233 A | 11/2000 | Owen et al. |
| 6,154,675 A | 11/2000 | Juran et al. |
| 6,216,036 B1 | 4/2001 | Jenkins et al. |
| 6,246,414 B1 | 6/2001 | Kawasaki |
| 6,249,705 B1 | 6/2001 | Snell |
| 6,278,890 B1 | 8/2001 | Chassaing et al. |
| 6,307,554 B1 | 10/2001 | Arai et al. |
| 6,308,102 B1 | 10/2001 | Sieracki et al. |
| 6,325,756 B1 | 12/2001 | Webb et al. |
| 6,345,200 B1 | 2/2002 | Mouchawar et al. |
| 6,442,432 B2 | 8/2002 | Lee |
| 6,525,727 B1 | 2/2003 | Junkins et al. |
| 6,564,104 B2 | 5/2003 | Nelson et al. |
| 6,587,104 B1 | 7/2003 | Hoppe |
| 6,611,267 B2 | 8/2003 | Migdal et al. |
| 6,622,048 B1 | 9/2003 | Mann et al. |
| 6,669,631 B2 | 12/2003 | Norris et al. |
| 6,786,405 B2 | 9/2004 | Wiedenhoefer |
| 6,852,080 B2 | 2/2005 | Bardy |
| 6,882,982 B2 | 4/2005 | McMenimen et al. |
| 6,895,280 B2 | 5/2005 | Meadows et al. |
| 6,920,360 B2 | 7/2005 | Lee et al. |
| 6,931,155 B1 | 8/2005 | Gioia |
| 6,961,448 B2 | 11/2005 | Nichols et al. |
| 6,961,617 B1 | 11/2005 | Snell |
| 7,003,349 B1 | 2/2006 | Andersson et al. |
| 7,034,823 B2 | 4/2006 | Dunnett |
| 7,058,453 B2 | 6/2006 | Nelson et al. |
| 7,060,030 B2 | 6/2006 | Von Arx et al. |
| 7,065,409 B2 | 6/2006 | Mazar |
| 7,066,910 B2 | 6/2006 | Bauhahn et al. |
| 7,076,303 B2 | 7/2006 | Linberg |
| 7,087,015 B1 | 8/2006 | Comrie et al. |
| 7,092,761 B1 | 8/2006 | Cappa et al. |
| 7,107,102 B2 | 9/2006 | Daignault et al. |
| 7,142,923 B2 | 11/2006 | North et al. |
| 7,181,286 B2 | 2/2007 | Sieracki et al. |
| 7,181,505 B2 | 2/2007 | Haller et al. |
| 7,184,837 B2 | 2/2007 | Goetz |
| 7,239,926 B2 | 7/2007 | Goetz |
| 7,257,446 B2 | 8/2007 | Mech et al. |
| 7,257,756 B2 | 8/2007 | Wolff et al. |
| 7,266,412 B2 | 9/2007 | Stypulkowski |
| 7,299,085 B2 | 11/2007 | Bergelson et al. |
| 7,359,751 B1 | 4/2008 | Erickson et al. |
| 7,373,204 B2 | 5/2008 | Gelfand et al. |
| 7,440,806 B1 | 10/2008 | Whitehurst et al. |
| 7,452,336 B2 | 11/2008 | Thompson |
| 7,463,927 B1 | 12/2008 | Chaouat |
| 7,474,223 B2 | 1/2009 | Nycz et al. |
| 7,481,759 B2 | 1/2009 | Whitehurst et al. |
| 7,489,970 B2 | 2/2009 | Lee et al. |
| 7,496,403 B2 | 2/2009 | Cao et al. |
| 7,499,048 B2 | 3/2009 | Sieracki et al. |
| 7,505,815 B2 | 3/2009 | Lee et al. |
| 7,551,960 B2 | 6/2009 | Forsberg et al. |
| 7,602,384 B2 | 10/2009 | Rosenberg et al. |
| 7,617,002 B2 | 11/2009 | Goetz |
| 7,627,372 B2 | 12/2009 | Vaisnys et al. |
| 7,640,059 B2 | 12/2009 | Forsberg et al. |
| 7,657,317 B2 | 2/2010 | Thacker et al. |
| 7,685,005 B2 | 3/2010 | Riff et al. |
| 7,711,603 B2 | 5/2010 | Vanker et al. |
| 7,720,549 B2 | 5/2010 | Schroeppel et al. |
| 7,747,330 B2 | 6/2010 | Nolan et al. |
| 7,774,067 B2 | 8/2010 | Keacher et al. |
| 7,778,710 B2 | 8/2010 | Propato |
| 7,801,596 B2 | 9/2010 | Fischell et al. |
| 7,801,611 B2 | 9/2010 | Persen et al. |
| 7,805,199 B2 | 9/2010 | Kenknight et al. |
| 7,822,483 B2 | 10/2010 | Stone et al. |
| 7,853,323 B2 | 12/2010 | Goetz |
| 7,885,712 B2 | 2/2011 | Goetz et al. |
| 7,890,180 B2 | 2/2011 | Quiles |
| 7,928,995 B2 | 4/2011 | Daignault |
| 7,934,508 B2 | 5/2011 | Behm |
| 7,940,933 B2 | 5/2011 | Corndorf |
| 7,953,492 B2 | 5/2011 | Corndorf |
| 7,953,612 B1 | 5/2011 | Palmese et al. |
| 7,957,808 B2 | 6/2011 | Dawant et al. |
| 7,978,062 B2 | 7/2011 | Lalonde et al. |
| 7,991,482 B2 | 8/2011 | Bradley |
| 8,014,863 B2 | 9/2011 | Zhang et al. |
| 8,021,298 B2 | 9/2011 | Baird et al. |
| 8,027,726 B2 | 9/2011 | Ternes |
| 8,046,241 B1 | 10/2011 | Dodson |
| 8,060,216 B2 | 11/2011 | Greenberg et al. |
| 8,068,915 B2 | 11/2011 | Lee et al. |
| 8,068,918 B2 | 11/2011 | Vallapureddy et al. |
| 8,078,440 B2 | 12/2011 | Otto et al. |
| 8,082,162 B2 | 12/2011 | Flood |
| 8,121,702 B2 | 2/2012 | King |
| 8,135,566 B2 | 3/2012 | Marshall et al. |
| 8,140,160 B2 | 3/2012 | Pless et al. |
| 8,140,167 B2 | 3/2012 | Donders et al. |
| 8,160,328 B2 | 4/2012 | Goetz et al. |
| 8,160,704 B2 | 4/2012 | Freeberg |
| 8,165,385 B2 | 4/2012 | Reeves et al. |
| 8,187,015 B2 | 5/2012 | Boyd et al. |
| 8,200,324 B2 | 6/2012 | Shen et al. |
| 8,200,340 B2 | 6/2012 | Skelton et al. |
| 8,219,206 B2 | 7/2012 | Skelton et al. |
| 8,233,991 B2 | 7/2012 | Woods et al. |
| 8,246,680 B2 | 8/2012 | Betz et al. |
| 8,249,713 B2 | 8/2012 | Fang et al. |
| 8,255,060 B2 | 8/2012 | Goetz et al. |
| 8,323,218 B2 | 12/2012 | Davis et al. |
| 8,326,433 B2 | 12/2012 | Blum et al. |
| 8,340,775 B1 | 12/2012 | Cullen et al. |
| 8,382,666 B1 | 2/2013 | Mao et al. |
| 8,386,032 B2 | 2/2013 | Bachinski et al. |
| 8,401,666 B2 | 3/2013 | Skelton et al. |
| 8,428,727 B2 | 4/2013 | Bolea et al. |
| 2001/0037220 A1 | 11/2001 | Merry et al. |
| 2003/0076301 A1 | 4/2003 | Tsuk et al. |
| 2003/0107572 A1 | 6/2003 | Smith et al. |
| 2003/0139652 A1 | 7/2003 | Kang et al. |
| 2003/0171911 A1 | 9/2003 | Fairweather |
| 2003/0177031 A1 | 9/2003 | Malek |
| 2003/0233129 A1 | 12/2003 | Matos et al. |

(56) References Cited

U.S. PATENT DOCUMENTS

| | | |
|---|---|---|
| 2004/0088374 A1 | 5/2004 | Webb et al. |
| 2004/0122477 A1 | 6/2004 | Whitehurst et al. |
| 2004/0210273 A1 | 10/2004 | Wang |
| 2005/0107831 A1 | 5/2005 | Hill et al. |
| 2005/0149356 A1 | 7/2005 | Cyr et al. |
| 2005/0168460 A1 | 8/2005 | Razdan et al. |
| 2005/0277872 A1 | 12/2005 | Colby et al. |
| 2006/0089888 A1 | 4/2006 | Roger |
| 2006/0095092 A1 | 5/2006 | Drew |
| 2006/0100832 A1 | 5/2006 | Bowman |
| 2006/0241720 A1 | 10/2006 | Woods et al. |
| 2006/0242159 A1 | 10/2006 | Bishop et al. |
| 2006/0282168 A1 | 12/2006 | Sherman et al. |
| 2007/0043585 A1 | 2/2007 | Matos |
| 2007/0078484 A1 | 4/2007 | Talarico et al. |
| 2007/0078497 A1 | 4/2007 | Vandanacker |
| 2007/0093998 A1 | 4/2007 | El-Baroudi |
| 2007/0179349 A1 | 8/2007 | Hoyme et al. |
| 2007/0203537 A1 | 8/2007 | Goetz et al. |
| 2007/0203538 A1 | 8/2007 | Stone et al. |
| 2007/0203543 A1 | 8/2007 | Stone et al. |
| 2007/0213790 A1 | 9/2007 | Nolan et al. |
| 2008/0004675 A1 | 1/2008 | King et al. |
| 2008/0033303 A1 | 2/2008 | Wariar et al. |
| 2008/0046036 A1 | 2/2008 | King et al. |
| 2008/0140161 A1 | 6/2008 | Goetz et al. |
| 2008/0177362 A1 | 7/2008 | Phillips et al. |
| 2008/0218517 A1 | 9/2008 | Holmdahl |
| 2008/0262565 A1 | 10/2008 | Bentwich |
| 2009/0018617 A1 | 1/2009 | Skelton et al. |
| 2009/0018619 A1 | 1/2009 | Skelton et al. |
| 2009/0024178 A1 | 1/2009 | Hennig |
| 2009/0048871 A1 | 2/2009 | Skomra |
| 2009/0089034 A1 | 4/2009 | Penney et al. |
| 2009/0099624 A1 | 4/2009 | Kokones et al. |
| 2009/0132009 A1 | 5/2009 | Torgerson |
| 2009/0136094 A1 | 5/2009 | Driver et al. |
| 2009/0196471 A1 | 8/2009 | Goetz et al. |
| 2009/0234873 A1 | 9/2009 | Li et al. |
| 2009/0264967 A1 | 10/2009 | Giftakis et al. |
| 2009/0281596 A1 | 11/2009 | King et al. |
| 2010/0004033 A1 | 1/2010 | Choe et al. |
| 2010/0010566 A1 | 1/2010 | Thacker et al. |
| 2010/0010574 A1 | 1/2010 | Skelton et al. |
| 2010/0010580 A1 | 1/2010 | Skelton et al. |
| 2010/0058462 A1 | 3/2010 | Chow |
| 2010/0076534 A1 | 3/2010 | Mock |
| 2010/0090004 A1 | 4/2010 | Sands et al. |
| 2010/0106475 A1 | 4/2010 | Smith et al. |
| 2010/0123547 A1 | 5/2010 | Stevenson et al. |
| 2010/0152534 A1 | 6/2010 | Kim et al. |
| 2010/0161345 A1 | 6/2010 | Cain et al. |
| 2010/0198103 A1 | 8/2010 | Meadows et al. |
| 2010/0198304 A1 | 8/2010 | Wang |
| 2010/0215277 A1 | 8/2010 | Huntington et al. |
| 2010/0222845 A1 | 9/2010 | Goetz |
| 2010/0223020 A1 | 9/2010 | Goetz |
| 2010/0265072 A1 | 10/2010 | Goetz et al. |
| 2010/0268304 A1 | 10/2010 | Matos |
| 2010/0280417 A1 | 11/2010 | Skelton et al. |
| 2010/0280578 A1 | 11/2010 | Skelton et al. |
| 2011/0004059 A1 | 1/2011 | Arneson et al. |
| 2011/0015514 A1 | 1/2011 | Skalli et al. |
| 2011/0015693 A1 | 1/2011 | Williamson |
| 2011/0023343 A1 | 2/2011 | Turner et al. |
| 2011/0038498 A1 | 2/2011 | Edgar |
| 2011/0040546 A1 | 2/2011 | Gerber et al. |
| 2011/0040547 A1 | 2/2011 | Gerber et al. |
| 2011/0046697 A1 | 2/2011 | Gerber et al. |
| 2011/0054560 A1 | 3/2011 | Rosenberg et al. |
| 2011/0054870 A1 | 3/2011 | Dariush et al. |
| 2011/0077459 A1 | 3/2011 | Rofougaran |
| 2011/0077616 A1 | 3/2011 | Bennett et al. |
| 2011/0093030 A1 | 4/2011 | Goetz et al. |
| 2011/0093047 A1 | 4/2011 | Davis et al. |
| 2011/0093051 A1 | 4/2011 | Davis et al. |
| 2011/0153341 A1 | 6/2011 | Diaz-Cortes |
| 2011/0170739 A1 | 7/2011 | Gillam et al. |
| 2011/0172564 A1 | 7/2011 | Drew |
| 2011/0172737 A1 | 7/2011 | Davis et al. |
| 2011/0172744 A1 | 7/2011 | Davis et al. |
| 2011/0185178 A1 | 7/2011 | Gotthardt |
| 2011/0191275 A1 | 8/2011 | Lujan et al. |
| 2011/0224523 A1 | 9/2011 | Budiman |
| 2011/0224665 A1 | 9/2011 | Crosby et al. |
| 2011/0246219 A1 | 10/2011 | Smith et al. |
| 2011/0264165 A1 | 10/2011 | Molnar et al. |
| 2011/0270358 A1 | 11/2011 | Davis et al. |
| 2011/0282414 A1 | 11/2011 | Kothandaraman et al. |
| 2011/0305376 A1 | 12/2011 | Neff |
| 2011/0307284 A1 | 12/2011 | Thompson et al. |
| 2011/0313268 A1 | 12/2011 | Kokones et al. |
| 2011/0313487 A1 | 12/2011 | Kokones et al. |
| 2012/0041518 A1 | 2/2012 | Kim et al. |
| 2012/0046715 A1 | 2/2012 | Moffitt et al. |
| 2012/0071947 A1 | 3/2012 | Gupta et al. |
| 2012/0083857 A1 | 4/2012 | Bradley et al. |
| 2012/0084689 A1 | 4/2012 | Ledet et al. |
| 2012/0089008 A1 | 4/2012 | Strehl et al. |
| 2012/0109230 A1 | 5/2012 | Kothandaraman et al. |
| 2012/0182244 A1 | 7/2012 | Arthur |
| 2012/0192874 A1 | 8/2012 | Bolea et al. |
| 2012/0215277 A1 | 8/2012 | Berg et al. |
| 2012/0215284 A1 | 8/2012 | Berg et al. |
| 2012/0239116 A1 | 9/2012 | Lee et al. |
| 2012/0256857 A1 | 10/2012 | Mak |
| 2012/0265269 A1 | 10/2012 | Lui et al. |
| 2012/0277828 A1 | 11/2012 | O'Connor et al. |
| 2012/0290041 A1 | 11/2012 | Kim et al. |
| 2012/0290272 A1 | 11/2012 | Bryan |
| 2012/0290976 A1 | 11/2012 | Lahm et al. |
| 2012/0296392 A1 | 11/2012 | Lee et al. |
| 2012/0296396 A1 | 11/2012 | Moffitt et al. |
| 2012/0296397 A1 | 11/2012 | Vansickle |
| 2012/0303087 A1 | 11/2012 | Moffitt et al. |
| 2012/0310300 A1 | 12/2012 | Kaula et al. |
| 2013/0023950 A1 | 1/2013 | Gauthier |
| 2013/0060299 A1 | 3/2013 | Polefko et al. |
| 2013/0060300 A1 | 3/2013 | Polefko et al. |
| 2013/0060301 A1 | 3/2013 | Polefko et al. |
| 2013/0060302 A1 | 3/2013 | Polefko et al. |
| 2013/0079848 A1 | 3/2013 | Campbell et al. |

FOREIGN PATENT DOCUMENTS

| | | |
|---|---|---|
| WO | 9959106 | 11/1999 |
| WO | 0209808 | 2/2002 |
| WO | 02084637 | 10/2002 |
| WO | 2009113102 | 9/2009 |
| WO | 2011028261 | 3/2011 |
| WO | 2011063248 | 5/2011 |
| WO | 2011104028 | 9/2011 |
| WO | 2011123669 | 10/2011 |
| WO | 2012018851 | 2/2012 |
| WO | 2012021862 | 2/2012 |
| WO | 2012135949 | 10/2012 |
| WO | 2013023085 | 2/2013 |

OTHER PUBLICATIONS

Extended EPSearch, "13179897", Dec. 13, 2013, 6 pgs.
Synamed, "Snyalink Features", Web Page, http://synamed.com/synalinkfeatures.html, 2010.

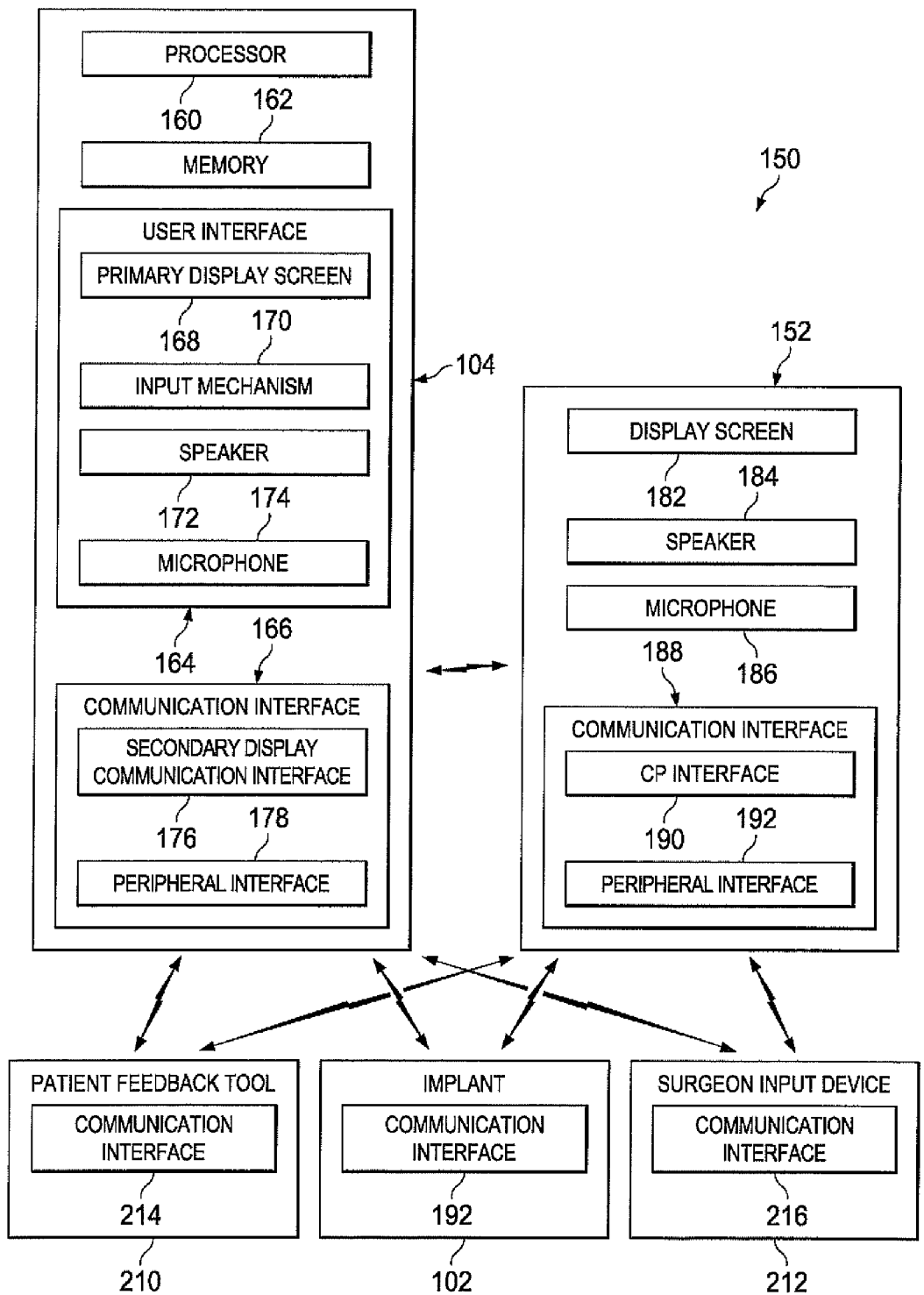

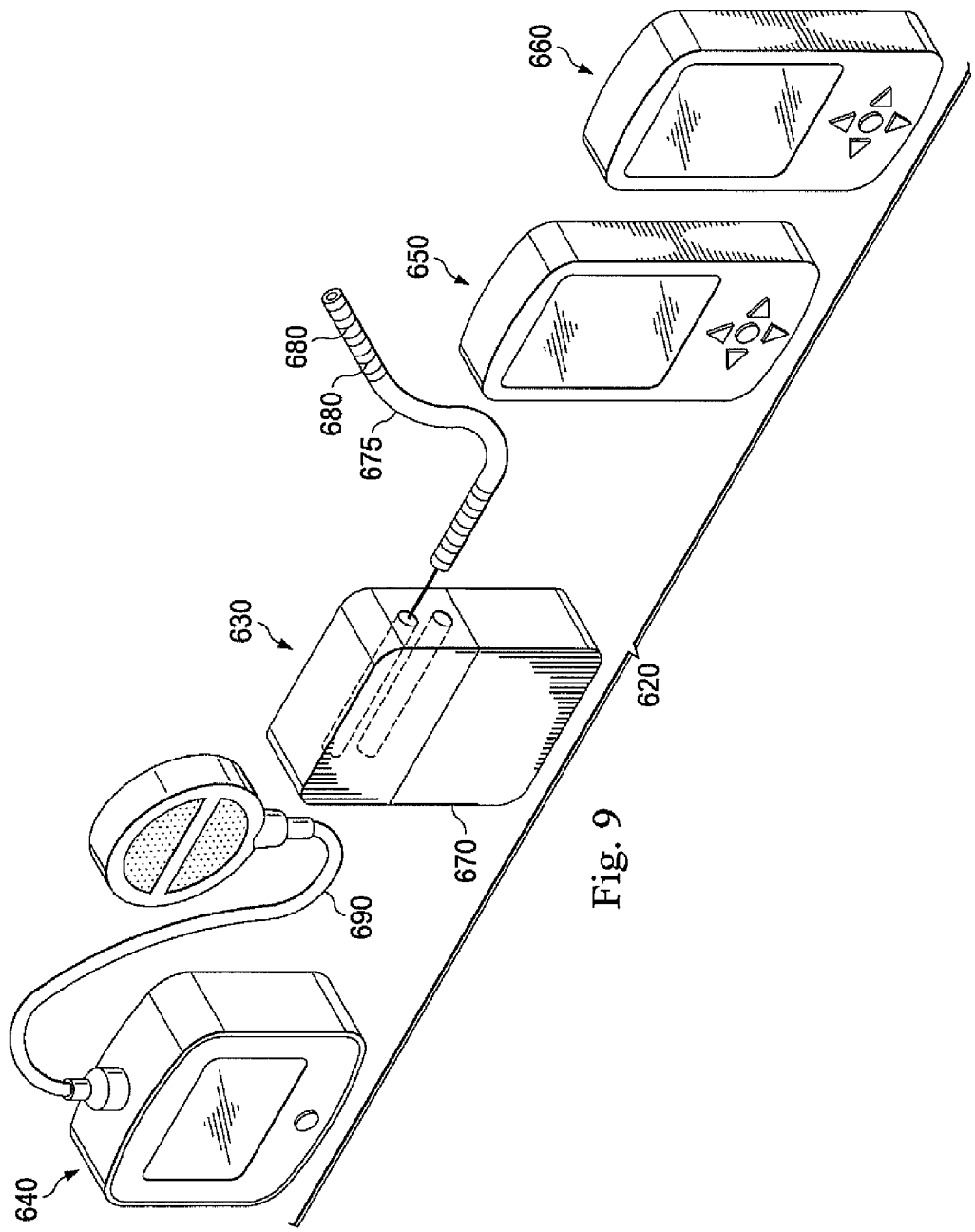

TOUCH SCREEN FINGER POSITION INDICATOR FOR A SPINAL CORD STIMULATION PROGRAMMING DEVICE

PRIORITY DATA

The present application is a divisional of U.S. patent application Ser. No. 14/011,156, filed on Aug. 27, 2013, now U.S. Pat. No. 9,180,302, which is a utility application of provisional U.S. patent application Ser. No. 61/695,394, filed on Aug. 31, 2012, entitled "Touch Screen Finger Position Indicator for a Spinal Cord Stimulation Programming Device," and a continuation-in-part (CIP) application of utility U.S. patent application Ser. No. 13/600,875, filed on Aug. 31, 2012, entitled "Clinician Programming System and Method", the disclosures of each which are hereby incorporated by reference in their entirety.

FIELD OF THE INVENTION

This disclosure is directed to an external monitor connection for a clinician programmer and the display of one or more simulated cursors.

BACKGROUND

Neurostimulation devices deliver therapy in the form of electrical stimulation pulses to treat symptoms and conditions, such as chronic pain, Parkinson's disease, or epilepsy, for example. Implantable neurostimulation devices, for example, deliver neurostimulation therapy via leads that include electrodes located proximate to the muscles and nerves of a patient.

Clinician programmers are used to control and program the neurostimulation devices with stimulation sequences to treat symptoms and conditions. These clinician programmers and devices of their type are relatively small to allow for easy transportation and storage. The portability has its price, however. It is difficult for more than one person to view the relatively small screen of a handheld programmer. People would have to crowd around the device to be able to attempt to see what is happening on the screen.

Further, even though the clinician programmer is portable, there are some areas where its use may be restricted. For instance, a clinician programmer may be covered under the drapes while a sales representative is talking to the patient. The clinician programmer thus may not be visible to the physician. As another example, the clinician programmer may not be a sterile device and cannot be taken into the sterile field in an operating room. Since the clinician programmer must remain outside of the sterile field, the physician is unable to read the screen while performing the procedure. Accordingly, the physician must verbally interact with and rely on someone (an external operator), who acts as his eyes and hands controlling the programmer outside of the sterile field. The situation could also be reversed, where the physician is doing the programming, and the staff is observing his/her actions, for example, talking to the patient at the head end of the surgery table. In any case, requiring an extra person results in additional time for the procedure to be completed as a result of the verbal communication of the programming device state and adjustments to be made between the physician and the external operator. The verbal interchange may also result in miscommunication which will add additional time to complete the procedure and possibly result in more severe consequences.

In addition, due to the small size of the clinician programmer, it may be difficult for users and observers to precisely identify an area of the screen (on the clinician programmer) where the user is performing data entry or other programming actions. In other words, users and observers may not know what part of the screen is being touched while the user is interacting with the user interface. Also, if device is coupled to an external monitor, observers will not know what part of the clinician screen is being touched by the user, especially if the external monitor and the observers are typically located in a separate room than the clinician programmer and the user.

The present disclosure is directed to devices, systems, and methods that address one or more deficiencies in the prior art.

SUMMARY

This disclosure is directed to a patient programmer in communication with an external monitor that helps to alleviate the problems set out above. When demonstrating the device, for example, the screen can be displayed on a large monitor for group viewing. In addition, when used for a procedure within an operating room, the programmer can be kept outside the sterile field, but its user interface can be made available for viewing by the physician and others through a projector or large screen monitor. In many cases, the external screen may be the only screen that the physician can see, because the clinician programmer is under the cover or tucked away.

In one exemplary aspect, the present disclosure is directed to a clinician programming system operable to control an implantable medical device. The clinician programming system includes a clinician programmer with a housing. The clinician programmer includes: a processor and memory having executable instructions enabling programming of an implantable pulse generator; a user interface configured to receive inputs by a clinician instructing operation of an implantable pulse generator; a first display configured to display information indicative of the inputs by the clinician or display information indicative of status of an implantable pulse generator, the first display having a first display size; an implant communication interface configured to transmit information from the clinician programmer to an implantable pulse generator and configured to receive information from an implantable pulse generator; and a display communication interface configured to transmit content shown on the display. The clinician programming system also includes a secondary unit separate from the housing of the clinician programmer, the secondary unit having a secondary display of a second display size, the secondary display being configured to communicate with the clinician programmer via the secondary display communication interface and configured to display information received via the secondary display communication interface. The secondary display may display information either mirrored or extended from the clinician programmer.

In one exemplary aspect, the present disclosure is directed to a clinician programmer. The clinician programmer includes a first display configured to display information to a user relating to an implantable device; a user input mechanism configured to receive inputs from the user controlling content shown on the first display; a secondary unit communication interface selectively attachable to a secondary unit, the secondary unit communication interface configured to transmit information to a secondary unit having a secondary display and configured to receive information for processing from the secondary unit; and a controller configured to receive a user input from the user input mechanism, the user input selecting a first mode that sends a display signal to the secondary display causing content shown on the secondary display to mirror or extend content shown on the first display and a second mode that sends a display signal to the secondary display causing content shown on the secondary display to differ from content shown on the primary display.

In one exemplary aspect, the present disclosure is directed to a clinician programmer. The clinician programmer includes a programming software module configured to generate a treatment program executable on an implantable medical device as a result of a user input; an implant communication interface configured to send the treatment program to an implantable medical device to operate the implantable device and configured to receive information from the implantable device; a primary display configured to display information relating to the treatment program; a secondary display unit communication interface configured to transmit information to a secondary display unit and configured to receive information from a secondary display unit; a microphone in communication with the secondary display unit communication interface and configured to capture audio from the user for transmission from the secondary display unit communication interface; and a speaker in communication with the a secondary display unit communication interface and configured to receive signals representing audio captured at the secondary display unit.

In one exemplary aspect, the present disclosure is directed to a surgical arrangement used when programming an implantable medical device. The surgical arrangement includes: a non-sterile (or wrapped sterile) clinician programmer having a memory storing instructional information for programming an implantable pulse generator and having a first display screen configured to display the instructional information to a user, the clinician programmer having a secondary display unit interface comprising a transmitter and a receiver configured to send display signals and configured to receive instructional signals; a secondary unit comprising a second display screen sized larger than the clinician programmer first display screen, the second display screen being disposed for viewing from a sterile room and connectable with the clinician programmer, the secondary unit being configured to receive the instructional information from the clinician programmer and display the instructional information on the second display screen under the instruction of the clinician programmer; and an implantable pulse generator in communication with one of the secondary unit and the clinician programmer, the implantable pulse generator having a memory and processor configured to activate electrodes based on information received from said one of the secondary unit and the clinician programmer, the implantable pulse generator being configured to electrically receive said information displayed relating to an electrode of the implantable pulse generator.

In one exemplary aspect, the present disclosure is directed to a method for performing trial stimulation during neurostimulator implant surgery. The method includes: providing a clinician programmer having a first display screen having a first display screen size; providing an external secondary unit having a second display screen having a second display screen size that is visible to medical personnel, for example operating room staff working within the sterile field; providing at least one stimulation lead operable to provide electrical stimulation to target tissue within a patient; connecting the clinician programmer to the external monitor; operating the clinician programmer to control the stimulation provided through the stimulation lead and to display information related to the stimulation on the external monitor; and displaying information relating to the stimulation lead on either one of the first and the second display screens, or both.

In one exemplary aspect, the present disclosure is directed to a method for programming an implantable device. The method includes: receiving an input at a user interface on a tablet-style clinician programmer; generating a first display signal on the clinician programmer that updates content on a first display based on the received user input, the first display having a first size; generating a second display signal for transmission to a secondary unit having a second display separate from the clinician programmer, the second display having a second size, wherein generating the second display signal includes enhancing the content of the second display signal to provide a clear image on the second size display; and transmitting the second display signal from the clinician programmer to the second display.

Yet another aspect of the present disclosure involves a clinician programmer. The clinician programmer includes: a touch-sensitive screen configured to display visual content to a user; one or more sensors configured to detect an engagement from the user with respect to the screen; a transceiver configured to conduct telecommunications with an external monitor that is multiple times larger than the clinician programmer; a memory storage component configured to store programming instructions; and a computer processor configured to execute the programming instructions to perform the following tasks: detecting, via the one or more sensors, the engagement from the user with respect to the screen; determining one or more locations on the screen corresponding to the user engagement; and sending signals, via the transceiver, to the external monitor to display one or more cursors on the external monitor, the one or more cursors graphically representing the one or more locations on the screen of the clinician programmer corresponding to the user engagement, respectively.

Another aspect of the present disclosure involves a medical system. The medical system includes: a monitor; and a clinician programmer located remotely from the monitor, the clinician programmer being configured to program parameters of an electrical stimulation therapy for a patient, the clinician programmer including: a touch-sensitive screen configured to display visual content to a user; one or more sensors configured to detect an engagement from the user with respect to the screen; a transceiver configured to conduct telecommunications with the monitor; a memory storage component configured to store programming instructions; and a computer processor configured to execute the programming instructions to perform the following tasks: detecting, via the one or more sensors, the engagement from the user with respect to the screen; determining one or more locations on the screen corresponding to the user engagement; and sending signals, via the transceiver, to the monitor to display one or more cursors on the monitor, the one or more cursors graphically representing the one or more locations on the screen of the clinician programmer corresponding to the user engagement, respectively.

Yet another aspect of the present disclosure involves a method of visualizing a user interaction with a clinician programmer. The method includes: detecting a user engagement with respect to a screen of the clinician programmer via one or more sensors associated with the screen of the clinician programmer; determining one or more locations on the screen of the clinician programmer corresponding to the user engagement; and displaying, via an external monitor communicatively coupled to the clinician programmer, one or more cursors that graphically represent the one or more locations on the screen of the clinician programmer corresponding to the user engagement, respectively.

Yet one more aspect of the present disclosure involves an apparatus for visualizing a user interaction. The apparatus includes: means for detecting a user engagement with respect to a screen of a clinician programmer, the clinician programmer being configured to program a pulse generator so that the pulse generator delivers an electrical stimulation therapy to a patient; means for determining one or more locations on the screen of the clinician programmer corresponding to the user engagement; and means for displaying or more cursors that graphically represent the one or more locations on the screen of the clinician programmer corresponding to the user engagement, respectively, wherein the means for the displaying is remotely located from, and communicatively coupled to, the clinician programmer.

BRIEF DESCRIPTION OF THE DRAWINGS

Aspects of the present disclosure are best understood from the following detailed description when read with the accompanying figures.

FIG. 2 is a block diagram showing an exemplary external monitor interface system in accordance with one aspect of the present disclosure.

FIG. 9 is a simplified block diagram of an example medical system according to various aspects of the present disclosure.

DETAILED DESCRIPTION

Figure 1A:
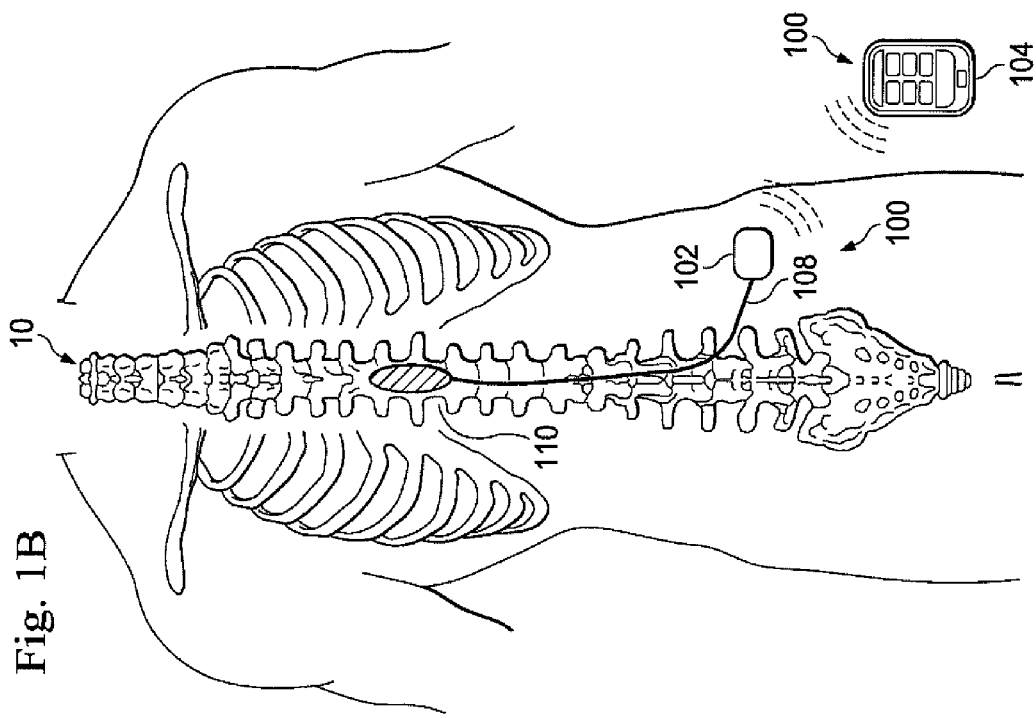
FIGS. 1A and 1B are illustrations of a patient's spine with an exemplary electrical stimulator treatment system disposed to treat a particular region of the spine in accordance with one aspect of the present disclosure.

The following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

The devices, systems, and methods described herein introduce an improved way for controlling and programming an implanted medical device. They use a clinician programmer ("CP") with a first display electrically coupled (for example, coupled in a wired or wireless manner) to a second display disposed for viewing by others than the clinician performing the programming. In one example, the CP may be outside a sterile field, but may be in communication with a display viewable to others who are within the sterile field. This may be particularly helpful to surgeons who perform surgeries and must issue instructions to a programming clinician to direct or control an implant in a certain manner. The surgeon may look at the second display and see the settings and programming as it occurs on the CP, instead of relying merely on verbal feedback from the programming clinician. This may streamline the surgery and since the surgeon can now see the clinician programming screen, may help assure the surgeon that his instructions are being carried out as requested without relying solely on verbal feedback. This may reduce verbal communication errors between staff during programming. Accordingly, this may provide a level of redundancy and risk management not achieved when programming is performed with only a CP outside the sterile field. In another example, the CP sends information shown on its display to the second larger display for viewing by additional people. This may be particularly helpful during training processes, when the clinician may be instructing trainees or other clinicians in treatment techniques, for example.

Figure 1B:
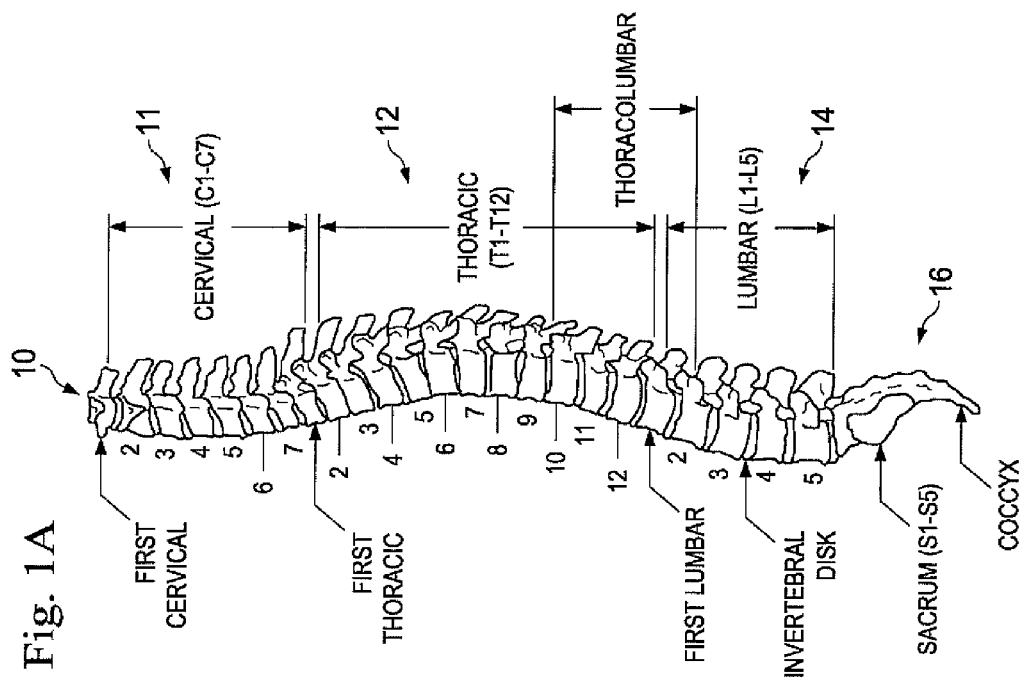

FIG. 1A is a side view of a spine 10, and FIG. 1B is a posterior view of the spine 10. FIG. 1B shows an exemplary electrical stimulator treatment system 100 disposed to treat a spinal region for treating a symptom, such as chronic pain. The system includes an implantable pulse generator (IPG) 102 that delivers electrical stimulation therapy to the patient, and a CP 104.

Referring now to FIGS. 1A and 1B, the spine 10 includes a cervical region 11, a thoracic region 12, a lumbar region 14, and a sacrococcygeal region 16. The cervical region 11 includes the top seven vertebrae, which may be designated with C1-C7. The thoracic region 12 includes the next twelve vertebrae below the cervical region 11, which may be designated with T1-T12. The lumbar region 14 includes the final five "true" vertebrae, which may be designated with L1-L5. The sacrococcygeal region 16 includes nine fused vertebrae that make up the sacrum and the coccyx. The fused vertebrae of the sacrum may be designated with S1-S5.

Neural tissue (not illustrated for the sake of simplicity) branches off from the spinal cord through spaces between the adjacent vertebrae. The neural tissue, along with the cord itself, can be individually and selectively stimulated in accordance with various aspects of the present disclosure. For example, referring to FIG. 1B, the IPG 102 is implanted inside the body. A conductive lead 108 is electrically coupled to the circuitry inside the IPG 102. The conductive lead 108 may be removably coupled to the IPG 102 through a connector, for example. A distal end of the conductive lead 108 is attached to one or more electrodes 110. In the example shown, the electrodes 110 are implanted adjacent to a desired nerve tissue in the thoracic region 12. The distal end of the lead 108 with its accompanying electrodes may be positioned beneath the dura mater using well-established and known techniques in the art.

The electrodes 110 deliver current drawn from the IPG 102, thereby generating an electric field near the neural tissue.

The electric field stimulates the neural tissue to accomplish its intended functions. For example, the neural stimulation may alleviate pain in an embodiment. In other embodiments, a stimulator as described above may be placed in different locations throughout the body and may be programmed to address a variety of problems, including for example but without limitation; prevention or reduction of epileptic seizures, bladder control, weight control or regulation of heart beats.

It is understood that the IPG 102, the lead 108, and the electrodes 110 may be implanted completely inside the body, or may have only one or more components implanted within the body while other components remain outside the body. When they are implanted inside the body, the implant location may be adjusted (e.g., anywhere along the spine 10) to deliver the intended therapeutic effects of spinal cord electrical stimulation in a desired region of the spine. The IPG 102 in this system is a fully implantable, battery-powered neurostimulation device for providing electrical stimulation to a body region of a patient. In some embodiments, an external pulse generator (EPG) is used. The EPG is identical to the IPG but the connection is done through percutaneous wires (communication may still be wireless though). In the example shown in FIG. 1B, the IPG 102 is configured to provide neural stimulation to the spine. However, in other embodiments, IPG 102 may be a different type of pulse generator, including, for example, a pacemaker, a defibrillator, a trial stimulator or any other type of medical device. Here, the IPG 102 is structurally configured and arranged for wireless programming and control through the skin of the patient. Accordingly, it includes a transmitter and receiver capable of communicating with external programming and control devices, such as the CP 104. It also includes a rechargeable power source, such as a battery configured to be wirelessly recharged through the patient's skin when a charger is externally placed in the proximity of the IPG 102.

The CP 104 is typically maintained in a health care provider's possession and can be used to program the IPG 102 as a part of the implantation treatment and later during office visits. For example only, the CP 104 can define the available stimulation programs for the IPG 102 by enabling and disabling particular stimulation programs, can define the actual stimulation programs by creating defined relationships between pulses, and perform other functions.

FIG. 2 is a block diagram showing an exemplary clinician programming system 150. The programming system 150 includes the CP 104, the IPG 102, a secondary display unit 152, a patient feedback tool ("PFT") 210, and a surgeon input device 212.

The CP 104 is, in one embodiment, a tablet-style device with a touch screen and radios for communicating with active implantable medical devices, such as neurostimulators like the IPG 102. As can be seen in FIG. 2, the CP 104 includes a processor 160, memory 162, a user interface 164, and a communication interface 166.

As shown in FIG. 2, the user interface 164 includes a primary display screen 168, an input mechanism 170, a speaker 172, and a microphone 174. The speaker 172 and the microphone 179 enable audio communication between the CP 104 and the secondary display unit 152. For example, the speaker 172 may be linked with a microphone 186 on the secondary display unit 152, and the microphone 174 may enable communication with a speaker 184 on the secondary display unit 152. As described below, this may be useful when the CP 104 and the secondary display unit 152 are in different locations.

The communication interface 166 enables the CP 104 to communicate with other components of the clinician programming system 150. In the embodiment shown, the communication interface 166 includes a secondary display communication interface 176 and a peripheral interface 178. These, along with other elements of the CP 104, are described in detail with reference to FIG. 3.

Figure 3:
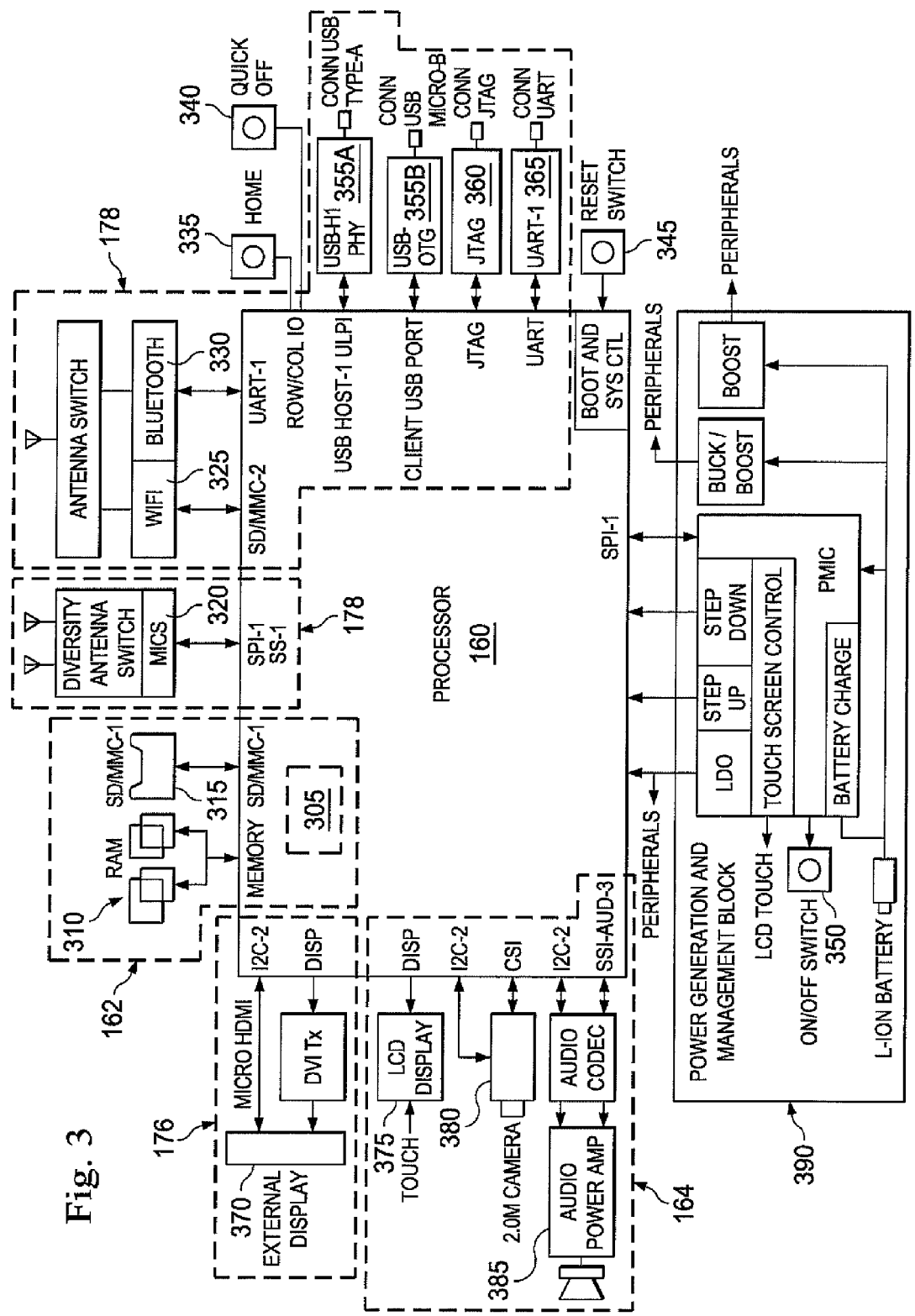
FIG. 3 is a block diagram of a clinician programmer for use in the exemplary external monitor interface system of FIG. 2.

FIG. 3 shows a block diagram of a more detailed construction of the CP 104. Referring to FIG. 3, the CP 104 includes a printed circuit board ("PCB") that is populated with a plurality of electrical and electronic components that provide power, operational control, and protection to the CP 104. The processor 160 is a controller for controlling the CP 104, and indirectly programming, controlling, and responding to the IPG 102, the secondary display unit 152, the PFT 210, and the surgeon input device 212. In one construction, the processor 160 is an applications processor model i.MX515 available from Freescale Semiconductor. More specifically, the i.MX515 applications processor has internal instruction and data caches, multimedia capabilities, external memory interfacing, and interfacing flexibility. Further information regarding the i.MX515 applications processor can be found in, for example, the "IMX510EC, Rev. 4" data sheet; dated August 2010; published by Freescale Semiconductor at www.freescale.com, the content of the data sheet being incorporated herein by reference. Of course, other processing units, such as other microprocessors, microcontrollers, digital signal processors, etc., can be used in place of the processor 160.

The CP 104 includes memory 162, which can be internal to the processor 160 (e.g., memory 305), external to the processor 160 (e.g., memory 310), or a combination of both. The memory 162 stores sets of instructional information with stimulation control parameters that are available to be selected for delivery through the communication interface 166 to the IPG 102 for electrical stimulation therapy or to the secondary display unit 152 for display to a plurality of individuals in the surgical area or elsewhere. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 160 executes software that is capable of being stored in the RAM (e.g., during execution), the ROM (e.g., on a generally permanent basis), or another non-transitory computer readable medium such as another memory or a disc. The CP 104 also includes input/output ("I/O") systems that include routines for transferring information between components within the processor 160 and other components of the CP 104 or external to the CP 104.

Software included in the implementation of the CP 104 is stored in the memory 305 of the processor 160, RAM 310, ROM 315, or external to the CP 104. The software includes, for example, firmware, one or more applications, program data, one or more program modules, and other executable instructions. The processor 160 is configured to retrieve from memory and execute, among other things, instructions related to the control processes and methods described below for the CP 104. For example, the processor 160 is configured to execute instructions retrieved from the memory 162 for establishing a protocol to control the IPG 102. Some embodiments include software modules configured to provide instructions for accomplishing particular tasks handled by the CP 104. For example, the CP 104 includes a programming software module configured to generate a treatment or stimulation program based on input received from a user of the CP 104. A secondary display software module controls the signals and communication sent from the CP 104 to the secondary display unit 152. Additional exemplary software will be described in further detail below.

Since the secondary display screen 182 is larger than the primary display screen 164 as described below, the secondary display software module may be configured to enhance the resolution or otherwise format or modify the display signal in a way that creates a clearer image of the content on the secondary display. This may ensure that a relatively clear image is shown on a secondary screen having a larger screen size than that of the CP primary display screen 164, while not requiring as high resolution for the smaller primary display screen 164.

One memory shown in FIG. 3 is memory 310, which can be a double data rate (DDR2) synchronous dynamic random access memory (SDRAM) for storing data relating to and captured during the operation of the CP 104. In addition, a secure digital (SD) multimedia card (MMC) can be coupled to the CP for transferring data from the CP to the memory card via slot 315. Of course, other types of data storage devices can be used in place of the data storage devices shown in FIG. 3.

The peripheral interface 178 is configured, depending on the embodiment, to receive data or signals from the IPG 102, the PFT 210, and the surgeon input device 212. Accordingly, it may include an implant communication interface, a PFT communication interface, and a surgeon input device communication interface. The implant communication interface includes structure and components enabling the CP 104 to send or receive information to and from the IPG 102. For example, it may comprise a radio transceiver that enables one-way or two-way communication with the IPG 102. The interface 178 may include components for wireless or wired communication and may be configured with any of the components discussed above with reference to the secondary display communication interface 176. In one example, the implant communication interface 178 comprises a medical implant communication service (MICS) RF transceiver used to communicate with the IPG 102 to communicate desired changes and to receive status updates from and relating to the IPG 102, such as battery status and any error information. In this example, the MICS RF transceiver utilizes a loop antenna for the communications with the IPG 102. Other antennas, such as, for example, dipole, chip antennas, or other antennas known in the art also may be used. The CP 104 may also include a programming interface used during manufacturing to load an operating system and program the CP 104.

The PFT communication interface and the surgeon input device communication interface may include structure and components enabling the CP to send and receive information to and from the PFT and the surgeon input device. These interfaces may be similar to that of the implant communication interface, or alternatively, may be otherwise enabled. Depending on the embodiment, the PFT communication interface and the surgeon input device communication interface may be one or more ports for wired communication, such as universal serial bus (USB) connectivity 355, including a Type A port and a Micro-B port; a related port for supporting Joint Test Action Group (JTAG) or other plug-in style port, or may be wireless using, for example, Wi-Fi portion 325 and Bluetooth portion 330 that respectively include a Wi-Fi communication interface, a Bluetooth communication interface, an antenna switch, and a related antenna all of which allows wireless communication following the Wi-Fi Alliance standard and Bluetooth Special Interest Group standard. Of course, other wireless local area network (WLAN) standards and wireless personal area networks (WPAN) standards can be used with the CP 104. Any other interface enabling communication between the CP 104 and the PFT 120 or surgeon input device 212 may be used. In some embodiments, the interface 178 is the same as the interface 176.

The secondary display communication interface 176 includes multiple bi-directional radio communication capabilities. Specific wireless portions included with the CP 104 are a Wi-Fi bi-direction radio communication portion 325, and a Bluetooth bi-direction radio communication portion 330. The Wi-Fi portion 325 and Bluetooth portion 330 include a Wi-Fi communication interface, a Bluetooth communication interface, an antenna switch, and a related antenna all of which allows wireless communication following the Wi-Fi Alliance standard and Bluetooth Special Interest Group standard. Of course, other wireless local area network (WLAN) standards and wireless personal area networks (WPAN) standards can be used with the CP 104.

The CP 104 includes multiple communication portions for wired communication. Exemplary circuitry and ports for receiving a wired connector include a port for supporting universal serial bus (USB) connectivity 355, including a Type A port and a Micro-B port, a portion and related port for supporting Joint Test Action Group (JTAG) connectivity 360, and a portion and related port for supporting universal asynchronous receiver/transmitter (UART) connectivity 365. Of course, other wired communication standards and connectivity can be used with or in place of the types shown in FIG. 3.

The secondary display communication interface 176 includes the structure and components enabling the CP 104 to send or receive information to and from the secondary display unit 152. In one embodiment, the secondary display communication interface 176 is integral with the CP 104 and is available along an edge, such as a lower edge, under a protective cover of the CP 104. In one embodiment, the secondary display communication interface 176 includes a HDMI port formed in a housing of the CP 104. The interface 176 may allow connection to the external secondary display unit 152 via a micro High-Definition Multimedia Interface (HDMI) 370, which provides a compact audio/video interface for transmitting uncompressed digital data to the external display unit 152. The use of the HDMI connection 370 allows the CP 104 to transmit video (and audio) communication to the external display unit 152. This may be beneficial in situations where others (e.g., the surgeon) may want to view the information being viewed by a CP user. The surgeon typically has no visual access to the CP 104 in the operating room. The HDMI connection 370 allows the surgeon to view information from the CP 104, thereby allowing greater communication between the clinician and the surgeon. For a specific example, the HDMI connection 370 can broadcast a high definition television signal that allows the surgeon to view the same information that is shown on the LCD (discussed below) of the CP 104. In addition, as HDMI signals are compatible with DVI, the CP 104 can also be connected, with the proper cabling, to other external display devices that only support DVI input. In some embodiments, audio and video can be played independently. In other embodiments, audio and video can be played in a synchronized manner.

In another embodiment, the secondary display communication interface 176 includes a wireless transmitter and receiver configured to wirelessly communicate with the secondary display communication interface 176. In one example, it includes structure and encoding for Wi-Fi communication. In another example, it includes structure and encoding for Bluetooth communication. Additional wireless protocols are contemplated. In some examples, the secondary display communication interface 176 is a networking port on the CP that enables the CP 104 to communicate with the secondary display unit 152 over a WAN, LAN, or other network, including the Internet.

The CP 104 includes three hard buttons: a "home" button 335 for returning the CP to a home screen for the device, a "quick off" button 340 for quickly deactivating stimulation, and a "reset" button 345 for rebooting the CP 104. The CP 104 also includes an "ON/OFF" switch 350, which is part of the power generation and management block (discussed below). In some embodiments, the "reset" button 345 may be eliminated, and the "ON/OFF" switch 350 can be used to remove all power when held long enough.

In FIG. 2, the CP 104 includes the primary display screen 168 arranged for viewing by the clinician operating the CP 104 and configured to display information relating to the programmer 104, the IPG 102, the secondary display unit 152, the PFT 210, and/or the surgeon input device 212. The input mechanism 170 permits a user to control images on the display and to make selections within a limited scope, so as to control the relationships between different control aspects. In FIG. 3, the primary display screen 168 and the input mechanism 170 are merged into a touch screen I/O device 375 for providing a user interface with the clinician. The touch screen display 375 can be a liquid crystal display (LCD) having a resistive, capacitive, or similar touch-screen technology. It is envisioned that multitouch capabilities can be used with the touch screen display 375 depending on the type of technology used. However, in place of a touch screen display, a computer keyboard, a standard pointing device, such as a mouse or trackball, or other input devices are also contemplated.

The CP 104 includes a camera 380 allowing the device to take pictures or video. The resulting image files can be used to document a procedure or an aspect of the procedure. For example, the camera 380 can be used to take pictures of barcodes associated with the IPG 102 or the leads 120, or documenting an aspect of the procedure, such as the positioning of the leads. Similarly, it is envisioned that the CP 104 can communicate with a fluoroscope or similar device to provide further documentation of the procedure. Other devices can be coupled to the CP 104 to provide further information, such as scanners or RFID detection. Similarly, the CP 104 includes an audio portion 385 having an audio codec circuit, audio power amplifier, and related speaker for providing audio communication to the user, such as the clinician or the surgeon.

The CP 104 further includes a power generation and management block 390. The power block 390 has a power source (e.g., a lithium-ion battery) and a power supply for providing multiple power voltages to the processor, LCD touch screen, and peripherals.

In one embodiment, the CP 104 is a handheld computing tablet with touch screen capabilities. The tablet is a portable personal computer with a touch screen, which is typically the primary input device. However, an external keyboard or mouse can be attached to the CP 104. The tablet allows for mobile functionality not associated with even typical laptop personal computers.

In operation, the IPG 102 (which may also be an EPG) through the use of the implanted medical electrical leads 108, and specifically the electrodes 110 (FIG. 1B), stimulates neurons of the spinal cord 10. The IPG 102 selects an electrode stimulating configuration, selects a stimulation waveform, regulates the amplitude of the electrical stimulation, controls the width and frequency of electrical pulses, and selects cathodic or anodic stimulation. This is accomplished by a healthcare professional (e.g., a clinician), using the CP 104, setting the parameters of the IPG 102. The setting of parameters of the IPG results in a "program," which is also referred to herein as a "protocol," for the electrode stimulation. Programming may result in multiple protocols that the patient can choose from. Multiple protocols allow, for example, the patient to find a best setting for paresthesia at a particular time of treatment.

Returning now to the block diagram in FIG. 2, the secondary display unit 152 includes a relatively large display screen suitable for displaying system information to a surgeon or patient when used in the operating room, to a group of students, or to other groups. In one example, the secondary display unit 152 is disposed within an operating surgical room where it can be seen by a surgeon performing a surgery. The secondary display unit 152 includes a display screen 182, a speaker 184, a microphone 186, and a communication interface 188. It is understood that the speaker 184 and the microphone 186 are optional and may be omitted in some embodiments.

Because the CP 104 is a portable device and includes a relatively small primary display screen 168, it is not easily viewed by multiple people at a single time. However, the display screen 182 of the secondary display unit 152 is sized larger than the display screen 168 of the primary CP 104 and enables multiple people to simultaneously view the screen and allows surgeons to see the IPG status or action taken by the CP. In one example, the display screen 182 is more than twice the size of the primary display screen 168 of the CP 104. One exemplary display screen 182 is sized with a diagonal measurement greater than about 22 inches. Another exemplary display screen 182 is sized with a diagonal measurement greater than about 30 inches. Other sizes, both larger and smaller are contemplated. The display screen, in some examples, is a large monitor whose image is controlled entirely from the clinician programmer 104. In one example it is a smart monitor configured to convert information received from the clinician into a three-dimensional image and to display information in a three-dimensional manner.

The speaker 184 and microphone 186 are linked respectively with the microphone 174 and the speaker 172 on the CP 104. As such, communication is enabled between individuals proximate the secondary display unit 152 and the individual proximate to and operating the CP 104. As indicated above, this may be useful when the CP 104 and the secondary display unit 152 are in different locations. In one embodiment, the communication via the microphones and the speakers on the CP 104 and the secondary display unit 152 communicate over the same secondary display communication interface 176 and the CP interface 190. In other embodiments, they have separate communication channels, wired or wireless, for transmitting and receiving information.

The communication interface 188 in the secondary display unit 152 includes a CP interface 190 and a peripheral interface 192. The CP interface 190 is configured, depending on the embodiment, to receive data or signals from the secondary display communication interface 176 on the CP 104. For example, the CP interface 190 may connect to the secondary display communication interface 176 on the CP 104 via HDMI using a Type D Micro to Type A HDMI connector. Alternatively, or in addition to, the HDMI signals may be compatible with DVI. Thus, the CP 104 can also be connected, with the proper cabling, to other external display devices that only support DVI input.

In one example, the secondary display unit is configured to display the same information as the primary display screen 168 on the CP 104. This mirroring of the screens 168, 182 enables a surgeon in an operating room and the clinician who is operating the CP to see the same information, albeit in different locations.

The peripheral interface 192 is configured, depending on the embodiment, to receive data or signals from the IPG 102, the PFT 210, and the surgeon input device 212. In one example, the peripheral interface 192 comprises a MICS RF transceiver used to communicate with the IPG 102, the PFT 210, and the surgeon input device 212. As described above, the MICS RF transceiver may utilize a loop antenna for its communications, with other antennas, such as, for example, dipole, chip antennas, or others known in the art also considered. For example, a communications link can be established between the IPG 102 and the secondary display unit 152, and communications can then occur over a MICS transceiver using a standard frequency for a medical device transmission.

The IPG 102 includes all the treatment information required for treating the patient condition with the electrodes 110, but also includes a communication interface 192. In one embodiment, the communication interface 192 is configured to communicate with one or both of the CP 104 and the secondary display unit 152 and convey information including IPG status, treatment status, program operation, and other information to the CP 104 and/or the secondary display unit 152. The secondary display unit 152, under the control of the CP 104, may communicate with the IPG communication interface 192 and may convey new treatment programs, including electrode management routines, such as activating particular electrodes in a particular order with a particular intensity, by varying amplitude, pulse width, and frequency. Once these treatment programs are received, the IPG 102 may execute or respond to the received information as directed by the clinician programmer 104 through the secondary display unit 152. In one example, the IPG 102 also communicates directly with the peripheral communication interface 178 of the CP 104. This embodiment may work well when the IPG 102 is in the proximity of the CP 104 and able to receive information via wireless or wired transmission.

The PFT 210 is sized to be held by a patient and can be used to provide feedback during programming of the IPG 102. In one example, the PFT 210 may be used to provide feedback to the CP 104 while a clinician operating the CP 104, under instruction from the surgeon, develops the protocol for the IPG 102. In one example, the PFT 210 is an ergonomic handheld device having a sensor (also referred to as input), a controller, and a communications output. The sensor can include a discrete switch and/or a continuously variable input, such as through the use of a thermocouple, strain gauge, pressure sensor, piezoelectric device, accelerometer, displacement mechanism, or other variable sensing mechanism. It is envisioned that the use of a continuously variable input can provide magnitude information, thereby providing improved feedback information from the patient.

The PFT 210 includes a communication interface 214 that communicates information to the communication interface 188 on the secondary display unit 152, which relays the information to the CP 104. For example, the communication interface 214 and the peripheral interface 192 may establish a communication link. Communications can then occur over Bluetooth or other wireless formats. The CP 104 may then, if appropriate, adjust the display imagery on one or both of the primary display screen 168 and the display screen 182 of the secondary display unit 152 to reflect the patient feedback.

The PFT 210 is used to help the surgeon program the IPG 102 based on patient feedback. For example in use, the CP 104 activates one or more of the electrodes (on leads that are connected to the IPG 102) in various patterns. When the patient feels a sensation as a result of a stimulus, such as a stimulus for paresthesia, he or she activates a sensor on the PFT 210. The activation of the sensor indicates to the clinician programming system 150 that the patient felt the stimulus and can also convey the degree of sensation that is felt, depending on the type of sensor that is employed. Given that there may be a delay from the time the patient feels a sensation and activates the sensor, the system 150 then re-stimulates the most recently-activated combinations of electrodes, and the patient again uses the PFT 210 to indicate when (and to what degree) a sensation is felt in order to determine the combination of electrodes to which the patient was reacting. Further description of methods for use of the PFT 210 is disclosed in U.S. patent application Ser. No. 13/118,781, filed on May 31, 2011, titled "Device to Provide Feedback For Neurostimulation Programming", the contents of which are incorporated herein by reference in its entirety.

Figure 4:
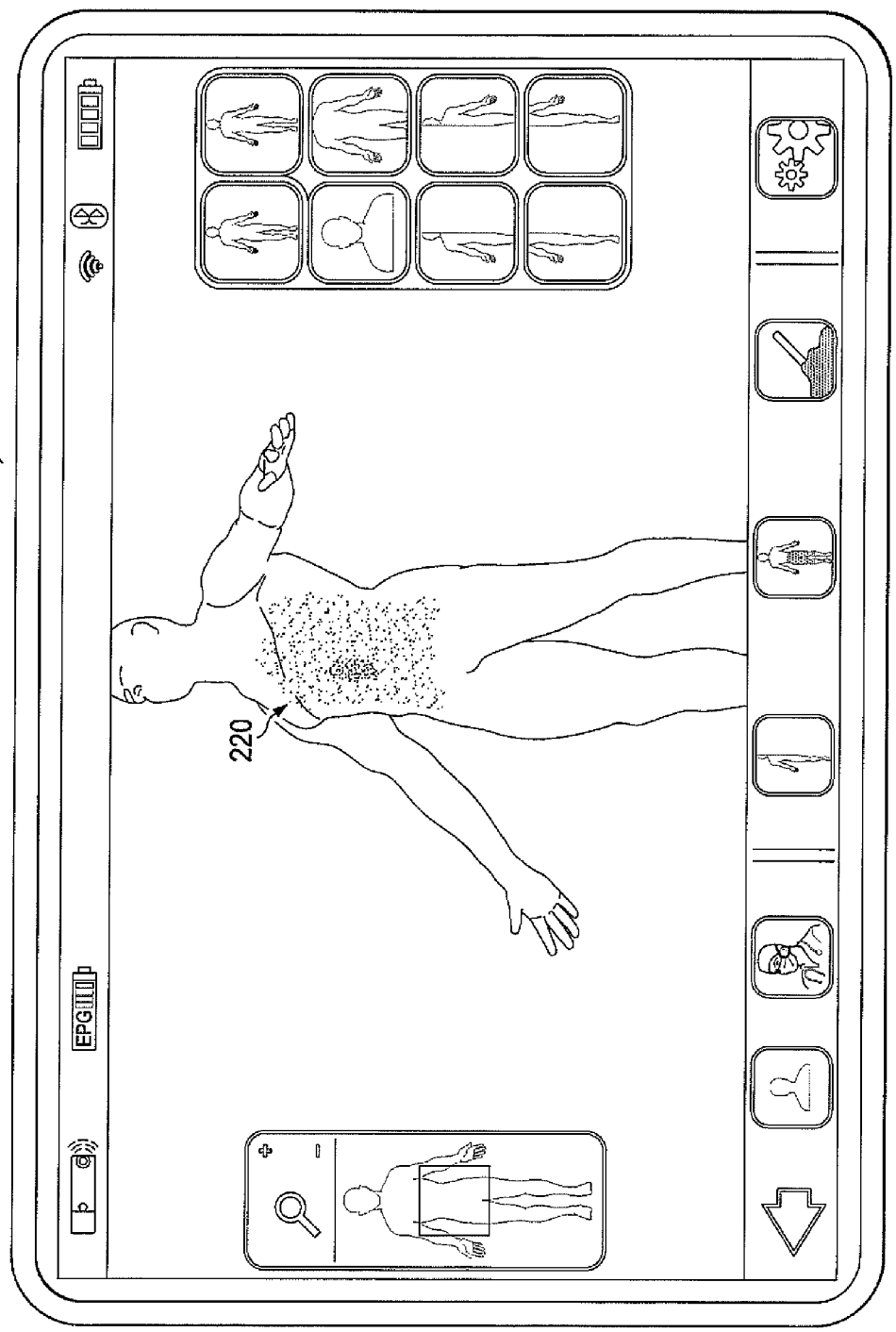
FIG. 4 is an exemplary user interface illustrating the generation of a pain map or a stimulation map.

In some embodiments, the patient may use the clinician programmer or another portable device (for example an electronic tablet or an electronic programmer) to draw a pain map and/or a stimulation map. For example, referring to FIG. 4, an exemplary user interface 215 illustrating the generation of a pain map or a stimulation map 220 is illustrated. The user interface 215 may be displayed through a touch-sensitive screen. The user interface 215 shows a three-dimensional model of a human body, which can be rotated and moved around. Using his fingers, the patient may be able to paint the pain/stimulation map 220 on a region of the human body to indicate the sensation he is experiencing in that region. During the painting process, the patient may choose the hue and the intensity of the color of the painted pain and stimulation regions to represent the various types of pain/stimulation or degrees of pain/stimulation. It is understood that the pain/stimulation map 220 may also be generated by a healthcare professional. The PFT 210 may be used to indicate the intensity of pain/stimulation, but the maps are displayed either on the clinician programmer (or tablet) or the external monitor.

Referring back to FIG. 2, the surgeon input device 212 is sized and configured to be held by the surgeon or other medical care provider within the sterile field in an operating room. Using it, the surgeon can control one or both of the CP 104 and the secondary display unit 152. The surgeon input device 212 may permit a surgeon to select particular images on the display screen 182 of the secondary display unit 152, which may be conveyed to the CP 104. In one embodiment, the CP allows a surgeon to select a particular electrode from an array of electrodes and to select activation including increasing and decreasing amplitude and frequency. This communication to the CP 104 through the secondary display unit 152 may help reduce the reliance on verbal cues and instructions passed to the clinician outside the sterile field, allowing the clinician to rely on more visual instructions simultaneously viewable by both the surgeon and the programming clinician. The surgeon input device 212 includes a communication interface 216 that communicates information to the communication interface 188 on the secondary display unit 152, which relays the information to the CP 104. For example, the communication interface 216 and the peripheral interface 192 may establish a communication link, and communications can then occur over a MICS transceiver using a standard frequency for a medical device transmission. The CP 104 may then, if appropriate, adjust the display imagery on one or both of the primary display screen 168 and the display screen 182 of the secondary display unit 152 to reflect the surgeon input.

In one aspect, this disclosure is directed to a method for displaying information on a CP to operating room staff working within a sterile field. One example of this will be described with reference to FIG. 5. The CP 104 is not a sterile device, so the external connection of the secondary display communication interface 176 may be used to display content shown on the primary display screen 168 of the CP 104 to those in the operating room while the CP 104 remains outside of the sterile field and outside the operating room. Making the content of the primary display screen 168 of the CP 104 viewable by the physician performing a procedure reduces the interaction required between a physician and the individual outside of the sterile field assisting the physician by performing the programming on the CP 104. The physician can easily see the operating state of the IPG 102 as shown on the CP 104 and does not require the individual assisting outside of the sterile field to describe it. Allowing the physician himself to see the actual information on the primary display screen 168 of the CP 104 reduces the time spent to perform the procedure, as well as reduce the occurrence of any miscommunications and any resulting undesirable consequences, for example reducing the probability of an infection.

Figure 5:
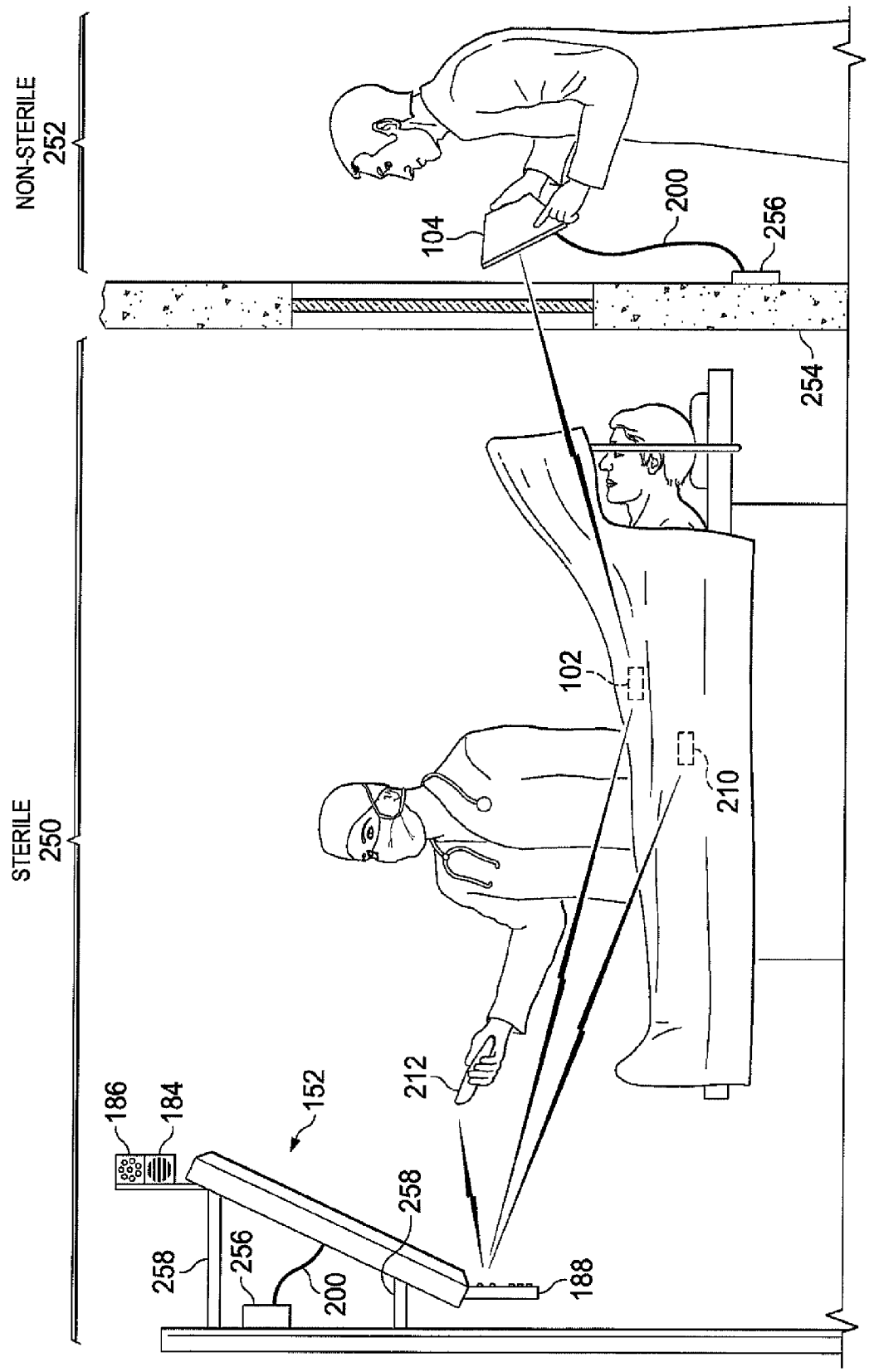
FIG. 5 is an illustration of an exemplary use of the exemplary external monitor interface system of FIG. 2 in accordance with one exemplary aspect of the present disclosure.

FIG. 5 shows an operating room 250 and a clinician room 252. These are separated by a physical barrier, shown here as a wall structure 254. The operating room 250 is or includes a sterile field. In the example, shown a surgeon performs a procedure on a patient having an implanted IPG 102, and a clinician stands in the clinician room 252 operating the CP 104. The patient holds the PFT 210, and the surgeon holds the surgeon input device 212. In this example, the CP 104 is disposed in the clinician room 252, and the secondary display unit 152 and the IPG 102 are disposed in the surgical room 250. In this embodiment, the CP 104 is a tablet controller fitted with a suitable communications port, for example a micro-HDMI connector. The CP 104 is able to drive a signal over the secondary display communication interface 176 of the CP 104 and copy the display from the primary display screen 168 on the CP 104 to the external secondary display screen 182 on the secondary display unit 152.

The secondary display unit 152 is, in this example, hung on a wall of the surgical room in a fixed location visible to the surgeon and his operating staff. In other examples, it may be visible to the surgeon and his operating staff through a window or other barrier. As can be seen, the secondary display unit 152 is much larger than the CP 104 and is configured to be easily viewable by several people at the same time. In one example, the secondary display screen 182 is at least double the size of the primary display screen 168 of the CP 104. The secondary display unit 152 includes the speaker 184, the microphone 186, and the communication interface 188. Verbal instructions from the surgeon to the clinician are captured at the microphone 186 and emitted from the speaker 172 on the CP 104. Likewise, verbal responses from the programmer can be captured by the microphone 174 on the CP 104 and heard though the speaker 184. In some embodiments, the contents of the screen of the CP 104 may also be broadcast via a suitable communications network.

In the example shown, the secondary display unit 152 is hung via a fixation structure 258. Here, the fixation structure 258 is a fixation bracket that extends from a rigid structure, such as the wall, and supports the secondary display unit 152 in a fixed position. As can be seen, the secondary display unit 152 is tipped at an angle to promote simple and convenient viewing from the sterile field in the surgical room. In this example it is spaced from the surgical area, and may not be a sterile device itself. It is operated without tactile feedback or input directly on the secondary display unit 152, and may be considered a hands-free device. It is controlled via the CP 104, but also may relay information collected from the IPG 102, the PFT 210, and the surgeon input device 212. Information is also relayed back from the secondary input to the CP display.

The communication interface 188 on the secondary display unit 152, and particularly the peripheral interface 192 communicates with one or more of the IPG 102, the PFT 210, and the surgeon input device 212. As indicated above, in one embodiment, the peripheral interface 192 provides two-way communication to each of these devices. In other examples, the peripheral interface 192 receives one-way communication from one or more of these devices. The communication interface 188 may be attached onto or otherwise carried on the display screen 182 or on or within its housing.

In the illustrated embodiment, a cable 200 extends from the secondary display communication interface 176 of the CP 104 to an outlet 256 shown on the wall structure 254. In this example, the secondary display communication interface 176 of the CP 104 is a micro-HDMI connector, and the cable 200 may be an HDMI cable extending between the secondary display communication interface 176 of the CP 104 and outlet 256.

The outlet 254 connects to an outlet 256 in the surgical room 250 via a cable within the wall, from which a cable extends to the secondary display unit 152. Over this wired line, the CP 104 communicates display information for presentation on the secondary display unit 152. That is, the CP 104 is able to drive a HDMI signal over the secondary display communication interface 176 of the CP 104 to copy the content from the primary display screen 168 on the CP 104 to the external display screen 182 on the secondary display unit 152. This can also be done via wireless communication. In other words, the wire 200 may not be needed in some embodiments, as the communication between the secondary display unit 152 and external devices are done wirelessly. In that case, the secondary display unit 152 may only need a power source or a battery.

In one example, the displayed content mirrors the information displayed on the CP 104. Accordingly, by viewing the secondary display unit 152, the surgeon sees the same information as the clinician operating the CP 104. In another example, the displayed content is different than or includes additional information than that displayed on the CP 104. Accordingly, with this extended display feature, the surgeon, by viewing the secondary display unit 152, sees different, but relevant information than the clinician operating the CP 104. In one example, the information shown on the CP 104 and/or the secondary display unit 152 includes IPG status information, charge information, program information, status and settings for one or more electrodes, including frequency, pulse width, and amplitude information for one or more electrodes. It may also include additional information. In one visualization of the patient's organs, x-ray information, or status of the patient's overall condition including items such as vital signs, including blood pressure, temperature, respiratory rates, heartbeat, and/or other vitals.

In one example, the secondary display unit 152 is connected to a Digital Video Interface (DVI) connector on the CP 104 and the content of the primary display screen 168 was cloned, copied, or replicated onto the display screen 182 of the secondary display unit 152 via the DVI interface. In one example, the system 150 achieves 30 frames per second (FPS) when outputting the primary display screen content to an 800.times.600 display screen 182. This is representative of the CP 104 because the data stream format output by the CP 104 over the HDMI interface may be nearly identical to that output from the DVI interface on the EVK.

In one example, the CP 104 requires the user to enable the secondary display screen 182 by selecting a display mode for the external display monitor 152. In one embodiment, the hardware for the secondary display communication interface 176 is arranged to detect when the external secondary display unit 152 is plugged in or otherwise connected. Using this functionality, the CP 104 may detect when the secondary display unit 152 is connected to the secondary display communication interface 176 of the CP 104, the driver in the CP 104 automatically switches to extending the display on the external monitor. Likewise, when the external secondary display unit 152 is detached, the CP 104 may disable the mirroring or extended display function.

Software modules on CP 104 provide instructions for accomplishing particular tasks handled by the CP 104. In the embodiment described above, the software includes a secondary display unit control module that controls the image generated on the secondary display screen 182. In one example, the module enables a user to select between two operating modes. For example, a first mode or mirroring mode may control the secondary display screen 182 to show content mimicking that shown on the primary display screen 164. In this mode, the CP 104 may generate display signals for transmission to the secondary display unit 152 so that the primary and secondary display screens show the same content. A second mode or extended display mode of the secondary display unit may control the secondary display screen 182 to show content different than that shown on the primary display screen 164. In this mode, the CP 104 may generate display signals for transmission to the secondary display unit 152 so that the primary and secondary display screens show different content, although some content may still overlap.

The ability to output the primary display screen display to an external, and notably, larger, secondary display unit 152, such as a large screen monitor or projector, provides a decided advantage when it comes to communicating instructions to and receiving verbal responses from a clinician outside the sterile field, such as in another room. The external secondary display unit 152 makes it much easier for the surgeon and others to view what is happening.

Figure 6:
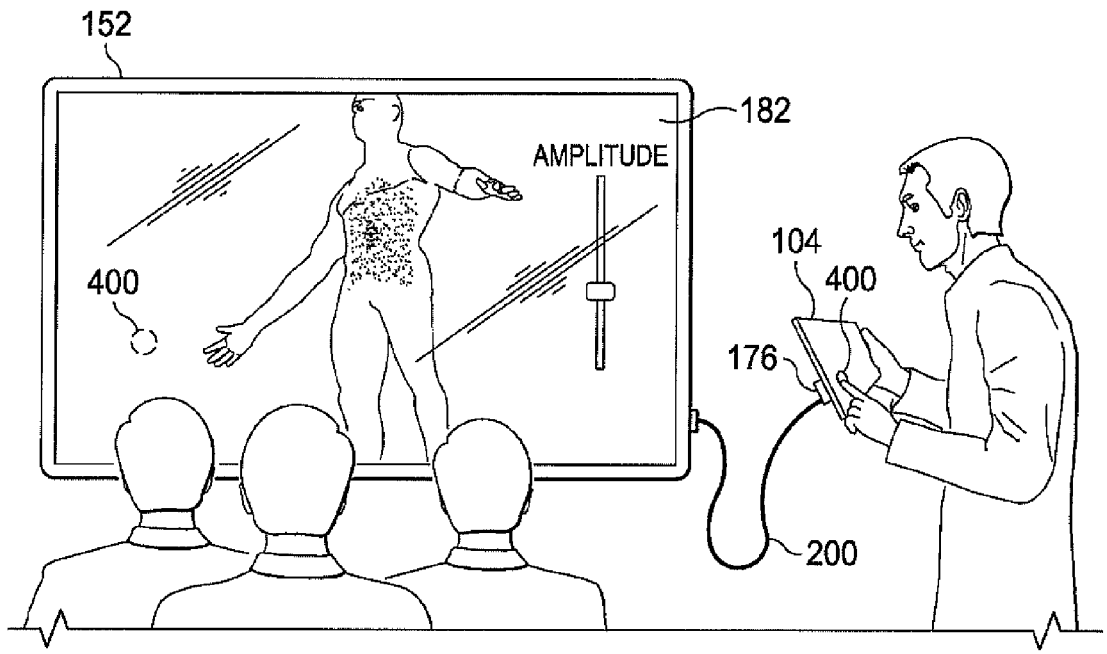
FIG. 6 is an illustration of an exemplary use of the exemplary external monitor interface system of FIG. 2 in accordance with one exemplary aspect of the present disclosure.

FIG. 6 shows another implementation of the system 150 according to one exemplary aspect of the present disclosure. In this example, the CP 104 and the secondary display unit 152 are illustrated being used to display an image to a number of individuals. The system illustrated may be used during instructional sessions, such as during training or education, for example.

In this embodiment, the CP 104 is a tablet controller fitted with a micro-HDMI connector, and the cable 200 is a HDMI cable extending between the secondary display communication interface 176 of the CP 104 and the communication interface 188 of the secondary display unit 152. The CP 104 is able to drive a HDMI signal over the secondary display communication interface 176 of the CP 104 and copies the display from the primary display screen 168 on the CP 104 to the external display screen 182 on the secondary display unit 152.

In this example, the display surfaces of the primary display screen 168 on the CP 104 and the external display screen 182 on the secondary display unit 152 are connected with Direct-Draw. Using the DirectDraw API, a screen copy is made of the primary display screen 168 on the CP 104. A copy of the primarily display screen 168 is then drawn to the secondary display screen's surface. In one example, the contents displayed on the secondary display screen 182 mirrors that of the primary displace seen 168. The software routine adds the ability for the screen to be copied automatically at a user defined rate and for the copying to be enabled or disabled as necessary.

As discussed above, the CP 104 may require the user to enable the secondary display screen 182 by selecting a display mode for the external display monitor 152, may be arranged to detect when the external secondary display unit 152 is plugged in or otherwise connected. The ability to output the primary display screen display to an external, and notably, larger, secondary display unit 152, such as a large screen monitor or projector, provides a decided advantage when it comes to training personnel because it is much easier for multiple people to view what is happening.

In one embodiment, the surgeon input device 212 is not a handheld device, but is a motion detector associated with the secondary display unit 152. In this embodiment, the secondary display unit 152 may include a light source and a camera or sensor to generate a depth map or other imagery of the surgeon or other health care provider in the operating room 250. By detecting surgeon movement, the surgeon input device 212 may receive inputs for controlling either the CP or features of the secondary input monitor 152. For example, a surgeon may be able to select a particular electrode or an array of electrodes using the motion detector and increase or decrease the amplitude and frequency of pulses from the electrode or electrode array to create a treatment program that may be loaded onto the IPG 102.

According to various aspects of the present disclosure, one or more cursors are displayed simultaneously both on the screen of the CP 104 and the secondary display screen 182 of the secondary display unit 152. For the sake of illustration, a cursor 400 is illustrated on both the screen of the CP 104 as well as on the secondary display screen 182. The cursor 400 corresponds to an area of the screen of the CP 104 engaged by the user (for example either through a finger or a stylus-like device). In some embodiments, the user engagement may be an actual touching of the area of the screen. In other embodiments, the user engagement may be a detected proximity to the area of the screen. The cursor 400 shown on the secondary display screen 182 tracks or mirrors the cursor 400 shown on the screen of the CP 104. Thus, as the user moves his finger or stylus to interactively engage with the screen of the CP 104, the audience can "see" exactly what the user is doing by looking at the secondary display unit 152 through the movement of the cursor 400 on the secondary display screen 182. It is understood that although one cursor 400 is illustrated herein (one on each display screen), a plurality of cursors may be displayed to correspond with multi-touch related user interactions in other embodiments. The cursor 400 will be discussed in more detail below with reference to FIGS. 8A-8B.

Figure 7:
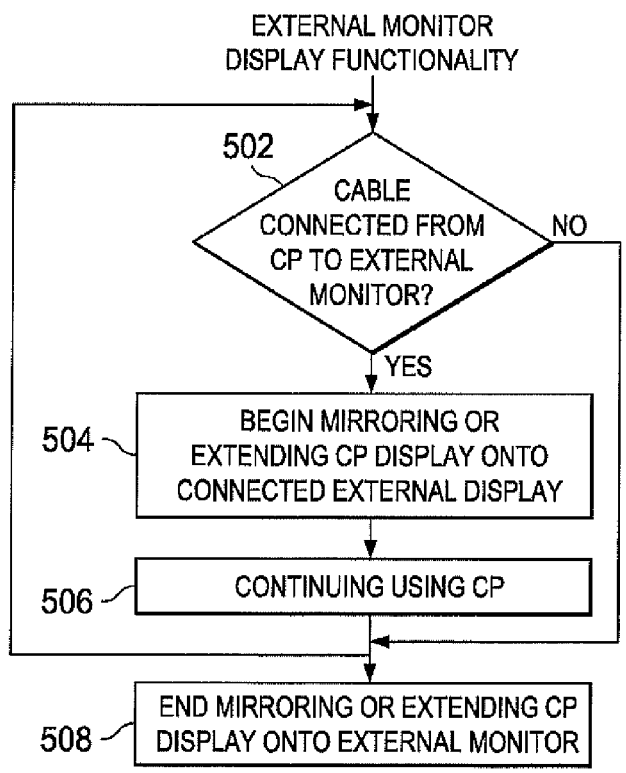
FIG. 7 is a flow chart showing an exemplary method of using the external monitor interface system of FIG. 2 in accordance with one exemplary aspect of the present disclosure.

FIG. 7 shows one method of activating the display functionality on the CP 104. The method includes querying whether the cable is connected for the CP to an external monitor, such as the secondary display unit 152, as indicated at step 502. If it is, then the CP 104 operates using control functionality that mirrors or extends the primary display screen 168 of the CP 104 onto the connected display screen 182 of the external display monitor 152, as indicated at a step 504. The cursor at touch points on the primary display screen 168 of the CP 104 would also be displayed on the display screen 182 of the external display monitor 152. At a step 506, the CP may be used to program the IPG 102 in the manner known in the art. Meanwhile the secondary display unit 152 continues to mirror or extend the display serene. This continues until the system determines at step 502 that the cable 200 is not connecting the CP 104 and the secondary display unit 152. If not connected, the CP is operates to end mirroring or extending CP display onto the secondary display unit 152. So long as the CP 104 is connected, the functionality of the secondary display unit 152 may be utilized. For example, in embodiments using the PFT 210 and/or the surgeon input device 212, the CP 104 is configured so that all functionality is enabled when the CP 104 and the secondary display unit 152 are connected.

In use, a clinician may take the cable 200 and plug it into the secondary display communication interface 176 of the CP 104. With this connection made the CP 104 can send display information to the secondary display unit 152 for display on the display screen 182. In one embodiment, over the same cable 200, feedback information from the secondary display unit 152 can be transmitted to the CP 104. This feedback information may be from the secondary display unit 152, or relayed through the secondary display unit 152 to the CP 104 from the PFT 210, the IPG 102, or the surgeon input device 212. In addition, the audio feed between the speakers and microphones on the CP 104 and the secondary display unit 152 may also be carried over the cable 200. In other embodiments, the system 150 includes a separate feedback line and/or a separate audio feed line. In yet another embodiment, the communication occurs wirelessly over a direct connection, between the CP 104 and the secondary display unit 152, such as, for example, through infra-red transmission, or over an indirect connection, such as through a wireless network.

The IPG 102 may then be implanted using methods and techniques known in the art. The surgeon may give instructions to the programmer of the CP 104 to activate or deactivate particular electrodes to develop a treatment program that provides a suitable level of relief to the patient. Since the surgeon can see the secondary display unit 152, he knows whether his instructions are being properly carried out without additional questions or explanation from the programmer of the CP 104. This reduction in reliance on verbal instructions may increase efficiently of the surgical procedure. Further, during the procedure, the surgeon may intervene or request additional views of displayed information using the surgeon input device 212. This allows the surgeon to have a level of control over the CP 104, although that level of control may be a lesser level than the level of control of the programmer of the CP 104. In one example, the surgeon input device may allow the surgeon to select an electrode and modify its frequency or amplitude of applied stimulation. Although the patient programmer is not sterile, the surgeon input device may be a sterile device, and in one embodiment, is a single-use device that is discarded after use.

During the programming process, information from the PFT 210 may be transmitted to the secondary display unit 152. The secondary display unit 152 may then relay the received information to the CP 104 for consideration or processing. Based on the patient feedback, the CP 104 may be controlled to update the images on the screens 164, 182 or provide additional information for programming the implant. Software on the CP 104 may control the images shown on the secondary display screen 182, as described above.

When a stimulation program is set, it may be transmitted to the IPG 102 either directly from the CP 104 or it may be transmitted to the secondary display unit for relay to the IPG 102. The IPG may then store the treatment program for operation.

Based on the discussions above, it can be seen that the clinician programmer and devices of its type are commonly used in a setting where a group of people is observing the actions of the user. Typically, the user (e.g., a clinician operating the clinician programmer 104 in FIGS. 5 and 6) is performing data entry or programming actions by using the touch screen provided by the clinician programmer. Because of the size of the clinician programmer, it may be difficult for the user and other observers to precisely identify the area of the screen on the clinician programmer where the user is performing the actions.

In these types of scenarios, users and observers don't know what part of the clinician programmer screen is being touched while the user is interacting with the user interface. Also, in situations where the clinician programmer is connected to an external monitor, such as the situation shown in FIGS. 5 and 6, observers don't know where the user is touching on the touch screen. In these situations, it is desirable to graphically indicate the location and pressure status of the user's finger or stylus on the touch screen of the clinician programmer, as that will provide additional feedback to the user and observers, thereby reducing errors such as input errors or other errors caused by miscommunication.

According to the various aspects of the present disclosure, one or more simulated cursors that are overlaid on top of user interface elements on the touch screen of the clinician programmer for indication of user interface interaction.

Figure 8A:
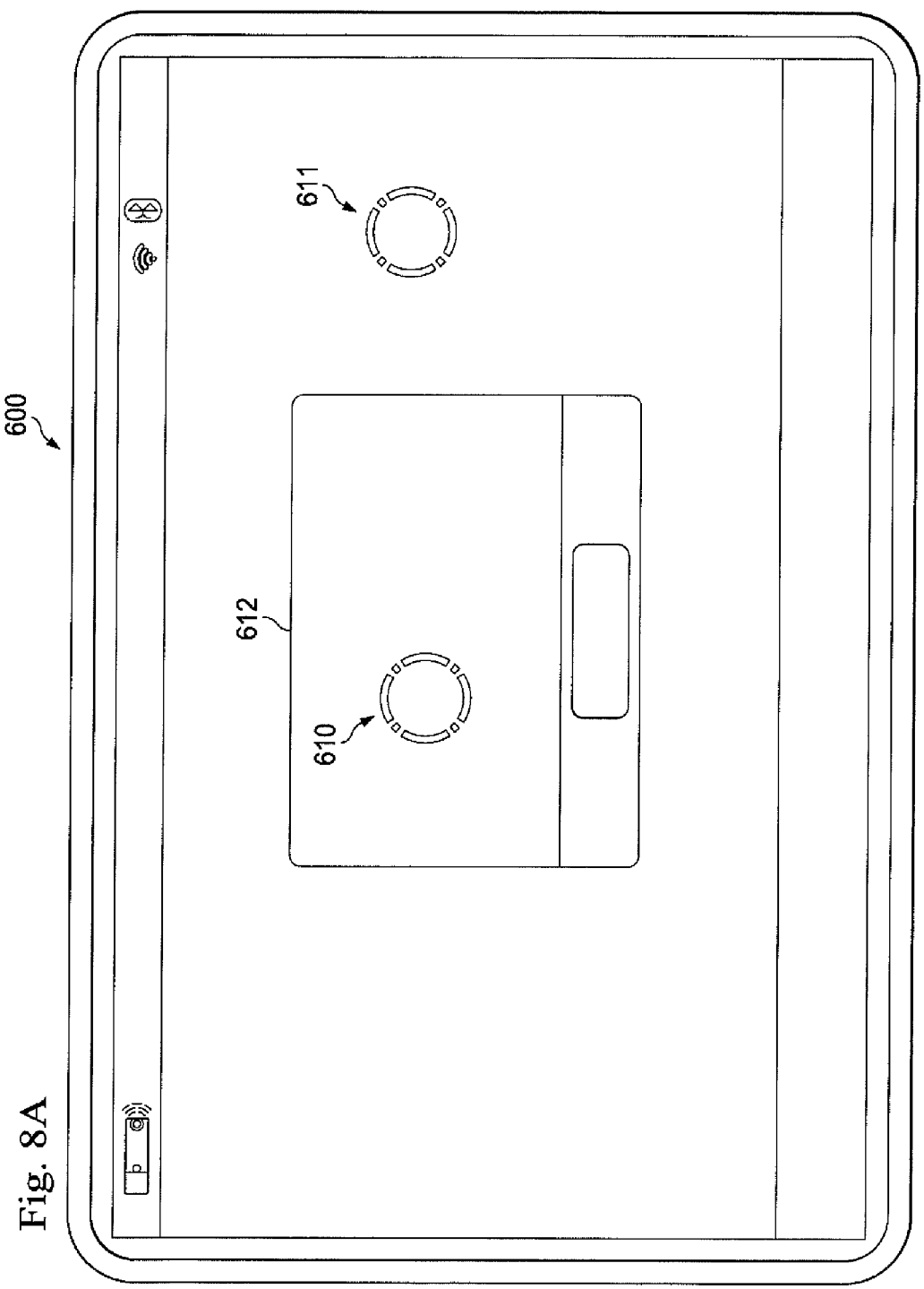
FIGS. 8A-8B are example user interfaces illustrating one or more simulated cursors in accordance with one exemplary aspect of the present disclosure.

Referring now to FIG. 8A, an example screen 600 of a clinician programmer (e.g., the screen of the clinician programmer 104 of FIGS. 5-6) is illustrated. The screen shows simulated cursors 610-611. In some embodiments, these simulated cursors 610-611 are displayed when the user's finger(s) or a stylus come into physical contact with the screen 600 of the clinician programmer. The physical contact between the user's finger(s) and the stylus and the screen 600 may be detected via touch screen sensors implemented on the clinician programmer. In other embodiments, these simulated cursors 610-611 are displayed when the user's finger(s) or a stylus do not come into physical contact with, but become very close to, the screen 600 of the clinician programmer. The physical proximity between the user's finger(s) and the stylus and the screen 600 may be detected via proximity sensors implemented on the clinician programmer.

The location of the simulated cursors 610-611 on the screen 600 corresponds to the location of the user's fingers or stylus. In the illustrated embodiment, more than one finger is detected, and therefore two simulated cursors 610-611 are displayed. Other numbers of fingers and/or styluses will result in their corresponding number of simulated cursors as well. In this manner, the clinician programmer of the present disclosure supports multi-touch functionalities. Multi-touch may refer to a touch sensitive interface's (e.g., the screen 600 of the clinician programmer) capability of detecting the presence of multiple points of contact with the interface. For example, the touch sensitive interface may be able to translate the detection of the engagement (or movement) of one finger with the interface as one command, but may translate the engagement (or movement) of two or three fingers with the interface as a different type of command. Styluses or other objects may also be used instead of, or in conjunction with, fingers in other embodiments.

The construction of the simulated cursors 610-611 is such that most of the area they cover is transparent to show other user interface elements that exist in the same area. For example, the simulated cursor 610 is disposed over a dialog box 612, but the content of the dialog box 612 is not substantially obstructed by the display of the simulated cursor 610. If the content of the dialog box 612 contained text, for example, the user may still be able to read such text even though portions of the text may be overlapping with the simulated cursor 610. Upon a detection that the user has disengaged the screen 600, for example by releasing the fingers or styluses, the user interface of the clinician programmer will go back to the default mode where no simulated cursors are being shown.

As discussed above, the clinician programmer can be electrically coupled to an external monitor such as the secondary display unit 152 of FIGS. 5-6, which may be remotely located from the clinician programmer. The external monitor can mirror the display of the clinician programmer's contents. According to the present disclosure, the simulated cursors 610-611 are also graphically displayed on the external monitor. The display of the simulated cursors 610-611 on the external monitor allows the observers to visualize what the user is doing with the clinician programmer.

In more detail, sometimes it may be physically impossible for the observers to see what part of the clinician programmer screen the user is touching. For example, the clinician programmer may be located outside the view of the observers, such as in the situation illustrated in FIG. 5, where the observer (e.g., a surgeon) is located in the same sterile room 250 as the secondary display unit 152 (i.e., remote external monitor), and the clinician programmer 104 and its user are located in a separate non-sterile room 252. In that scenario, even though the secondary display unit 152 can mirror the graphical display of the clinician programmer 104, the surgeon cannot see what parts of the clinician programmer are being engaged by the user's fingers or stylus.

Even if the observers are in the same room as the user and the clinician programmer, it is difficult for a group of observers to all get within close proximity to the user and see how the user is using the clinician programmer (e.g., entering programming parameters). First, it may not be feasible for a group of observers to be all crowded near the user, since space around the user may be constricted, and the crowding around the user may interfere with the user programming. Second, even if the observers all manage to get within viewing distance of the clinician programmer, the relatively small size of the clinician programmer means that the observers may not see (at least not clearly) exactly where on the clinician programmer screen the user is touching.

According to the present disclosure, the simulated cursors 610-611 shown in FIG. 8A provide a visual indication as to where the user's finger or stylus is. Even if the observers are located in a separate room from the clinician programmer, they can still see the display and movements of the simulated cursors 610-611 on the external monitor. Since the simulated cursors 610-611 track the position and movements of the clinician programmer user's fingers or styluses, the observers will know what parts of the clinician programmer are being engaged by the user and will understand the user's actions more clearly. Consequently, potential miscommunication between the user and the observers is reduced.

Figure 8B:
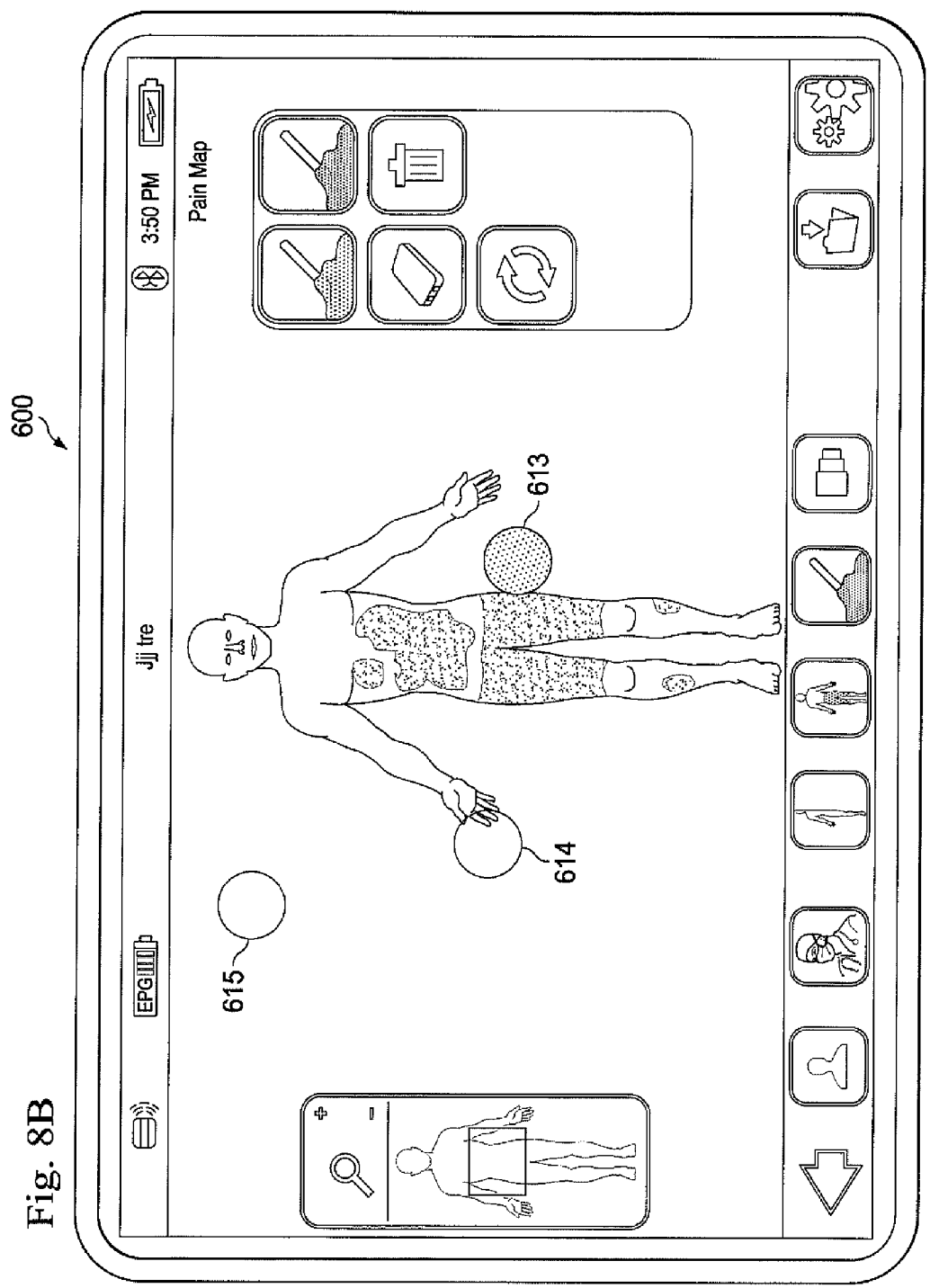

In addition to showing the position of the user's fingers or styluses on the screen 600 or external monitor, the simulated cursors 610-611 can also portray the action of selecting or tapping on the touch screen 600 by changing the color of one or more of the simulated cursors 610-611 or highlighting one or more of the simulated cursors 610-611 for a limited amount of time. For example, as shown in FIG. 8B, three fingers (or styluses or other objects) are detected in proximity of the screen 600 or touching the screen. Only one finger invoked an action, for example by actually touching the touch screen 600, while the other two fingers are merely in proximity with but not touching the touch screen 600. As a result, a simulated cursor 613 associated with the finger that invoked the action is highlighted temporarily while the remaining two simulated cursors 614-615 (associated with the fingers in proximity of the touch screen 600) remain in their original state. In other words, the simulated cursor 613 is triggered by activating a touch sensor on the clinician programmer, while the simulated cursors 614-615 are triggered by activating proximity sensors on the clinician programmer.

In the embodiment illustrated, the simulated cursor 613 is highlighted with an orange color, while the other two simulated cursors 614-615 are not colored (or assume the same color as the color of the background in the touch screen 600). Of course, the simulated cursor 613 may be visually differentiated from the simulated cursors 614-615 via other approaches or techniques in other embodiments. For example, instead of representing the simulated cursors 613 and 614-615 with different colors, they may be visually differentiated with different sizes or shapes, or different associated texts, or by different animations (for example the simulated cursor 613 may be flashing/flickering while the other simulated cursors 614-615 remain static) in various alternative embodiments. In any case, the visual differentiation among the simulated cursors allows the user or observers to distinguish between simulated indicators that are tracking the detected fingers from the one finger that invoked an action on the CP.

FIG. 9 is a simplified block diagram of a medical device system 620 is illustrated to provide an example context of the various aspects of the present disclosure. The medical system 620 includes an implantable medical device 630, an external charger 640, a patient programmer 560, and a clinician programmer 660. The implantable medical device 630 can be implanted in a patient's body tissue. In the illustrated embodiment, the implantable medical device 630 includes an implanted pulse generator (IPG) 670 that is coupled to one end of an implanted lead 675. The other end of the implanted lead 675 includes multiple electrode surfaces 680 through which electrical current is applied to a desired part of a body tissue of a patient. The implanted lead 675 incorporates electrical conductors to provide a path for that current to travel to the body tissue from the IPG 670. Although only one implanted lead 675 is shown in FIG. 9, it is understood that a plurality of implanted leads may be attached to the IPG 670.

Although an IPG is used here as an example, it is understood that the various aspects of the present disclosure apply to an external pulse generator (EPG) as well. An EPG is intended to be worn externally to the patient's body. The EPG connects to one end (referred to as a connection end) of one or more percutaneous, or skin-penetrating, leads. The other end (referred to as a stimulating end) of the percutaneous lead is implanted within the body and incorporates multiple electrode surfaces analogous in function and use to those of an implanted lead.

The external charger 640 of the medical device system 620 provides electrical power to the IPG 670. The electrical power may be delivered through a charging coil 690. In some embodiments, the charging coil can also be an internal component of the external charger 640. The IPG 670 may also incorporate power-storage components such as a battery or capacitor so that it may be powered independently of the external charger 640 for a period of time, for example from a day to a month, depending on the power requirements of the therapeutic electrical stimulation delivered by the IPG.

The patient programmer 650 and the clinician programmer 660 may be portable handheld devices that can be used to configure the IPG 670 so that the IPG 670 can operate in a certain way. The patient programmer 650 is used by the patient in whom the IPG 670 is implanted. The patient may adjust the parameters of the stimulation, such as by selecting a program, changing its amplitude, frequency, and other parameters, and by turning stimulation on and off. The clinician programmer 660 is used by a medical personnel to configure the other system components and to adjust stimulation parameters that the patient is not permitted to control, such as by setting up stimulation programs among which the patient may choose, selecting the active set of electrode surfaces in a given program, and by setting upper and lower limits for the patient's adjustments of amplitude, frequency, and other parameters.

In the embodiments discussed below, the clinician programmer 660 is used as an example of the electronic programmer. However, it is understood that the electronic programmer may also be the patient programmer 650 or other touch screen programming devices (such as smart-phones or tablet computers) in other embodiments.

Figure 10:
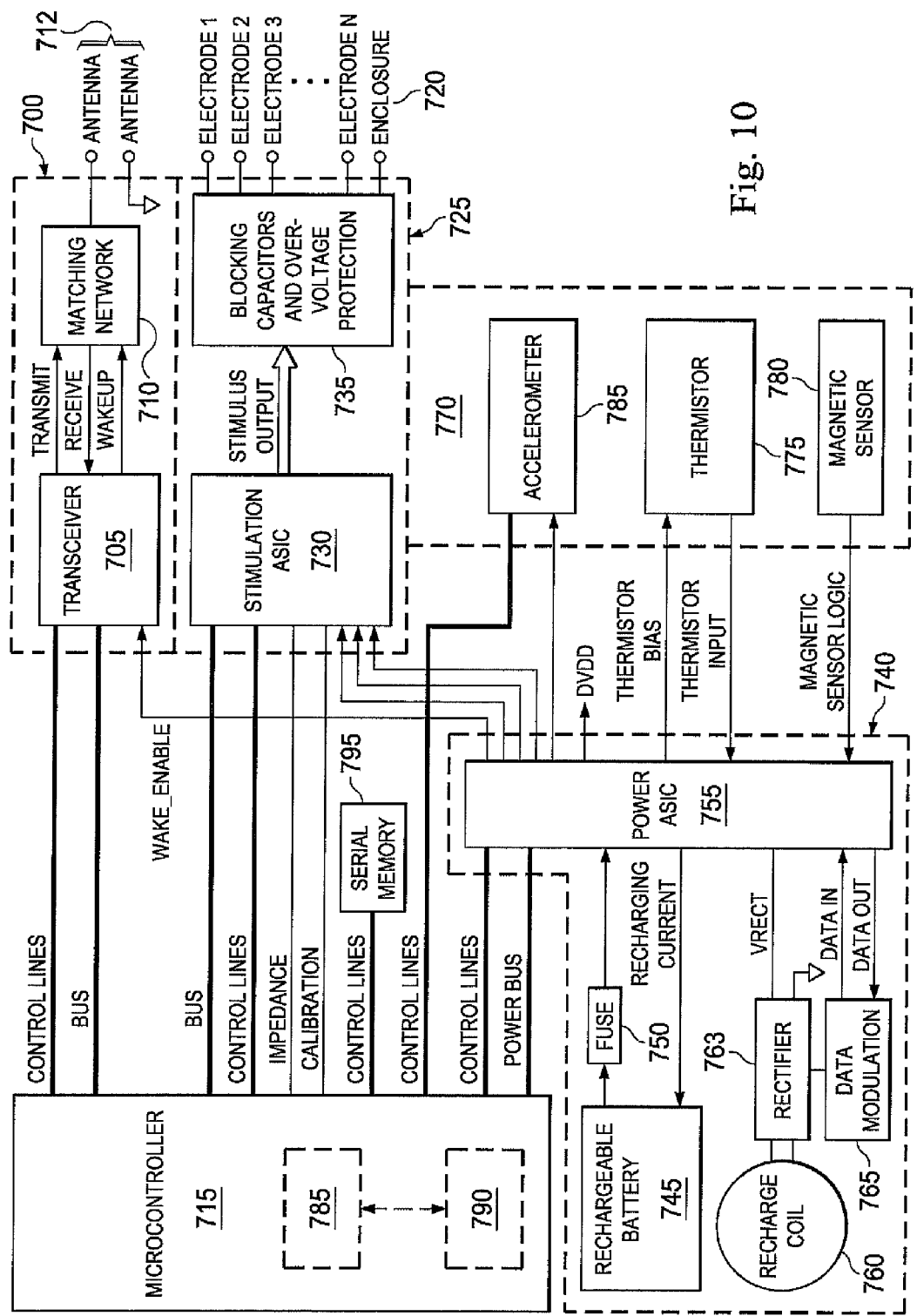
FIG. 10 is a simplified block diagram of an implantable medical device according to various aspects of the present disclosure.

FIG. 10 shows a block diagram of one embodiment of an implantable medical device. In the embodiment shown in FIG. 10, the implantable medical device includes an implantable pulse generator (IPG). The IPG includes a printed circuit board ("PCB") that is populated with a plurality of electrical and electronic components that provide power, operational control, and protection to the IPG. With reference to FIG. 10, the IPG includes a communication portion 700 having a transceiver 705, a matching network 710, and antenna 712. The communication portion 700 receives power from a power ASIC (discussed below), and communicates information to/from the microcontroller 715 and a device (e.g., the CP) external to the IPG. For example, the IPG can provide bi-direction radio communication capabilities, including Medical Implant Communication Service (MICS) bi-direction radio communication following the MICS specification.

The IPG provides stimuli to electrodes of an implanted medical electrical lead (not illustrated herein). As shown in FIG. 10, N electrodes are connected to the IPG. In addition, the enclosure or housing 720 of the IPG can act as an electrode. The stimuli are provided by a stimulation portion 225 in response to commands from the microcontroller 215. The stimulation portion 725 includes a stimulation application specific integrated circuit (ASIC) 730 and circuitry including blocking capacitors and an over-voltage protection circuit. As is well known, an ASIC is an integrated circuit customized for a particular use, rather than for general purpose use. ASICs often include processors, memory blocks including ROM, RAM, EEPROM, FLASH, etc. The stimulation ASIC 730 can include a processor, memory, and firmware for storing preset pulses and protocols that can be selected via the microcontroller 715. The providing of the pulses to the electrodes is controlled through the use of a waveform generator and amplitude multiplier of the stimulation ASIC 730, and the blocking capacitors and overvoltage protection circuitry 735 of the stimulation portion 725, as is known in the art. The stimulation portion 725 of the IPG receives power from the power ASIC (discussed below). The stimulation ASIC 730 also provides signals to the microcontroller 715. More specifically, the stimulation ASIC 730 can provide impedance values for the channels associated with the electrodes, and also communicate calibration information with the microcontroller 715 during calibration of the IPG.

The IPG also includes a power supply portion 740. The power supply portion includes a rechargeable battery 745, fuse 750, power ASIC 755, recharge coil 760, rectifier 763 and data modulation circuit 765. The rechargeable battery 745 provides a power source for the power supply portion 740. The recharge coil 760 receives a wireless signal from the PPC. The wireless signal includes an energy that is converted and conditioned to a power signal by the rectifier 763. The power signal is provided to the rechargeable battery 745 via the power ASIC 755. The power ASIC 755 manages the power for the IPG. The power ASIC 755 provides one or more voltages to the other electrical and electronic circuits of the IPG. The data modulation circuit 765 controls the charging process.

The IPG also includes a magnetic sensor 780. The magnetic sensor 780 provides a "hard" switch upon sensing a magnet for a defined period. The signal from the magnetic sensor 780 can provide an override for the IPG if a fault is occurring with the IPG and is not responding to other controllers.

The IPG is shown in FIG. 10 as having a microcontroller 715. Generally speaking, the microcontroller 715 is a controller for controlling the IPG. The microcontroller 715 includes a suitable programmable portion 785 (e.g., a microprocessor or a digital signal processor), a memory 790, and a bus or other communication lines. An exemplary microcontroller capable of being used with the IPG is a model MSP430 ultra-low power, mixed signal processor by Texas Instruments. More specifically, the MSP430 mixed signal processor has internal RAM and flash memories, an internal clock, and peripheral interface capabilities. Further information regarding the MSP 430 mixed signal processor can be found in, for example, the "MSP430G2x32, MSP430G2x02 MIXED SIGNAL MICROCONTROLLER" data sheet; dated December 2010, published by Texas Instruments at www.ti.com; the content of the data sheet being incorporated herein by reference.

The IPG includes memory, which can be internal to the control device (such as memory 790), external to the control device (such as serial memory 795), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The programmable portion 785 executes software that is capable of being stored in the RAM (e.g., during execution), the ROM (e.g., on a generally permanent basis), or another non-transitory computer readable medium such as another memory or a disc.

Software included in the implementation of the IPG is stored in the memory 790. The software includes, for example, firmware, one or more applications, program data, one or more program modules, and other executable instructions. The programmable portion 785 is configured to retrieve from memory and execute, among other things, instructions related to the control processes and methods described below for the IPG. For example, the programmable portion 285 is configured to execute instructions retrieved from the memory 790 for sweeping the electrodes in response to a signal from the CP.

Figure 11:
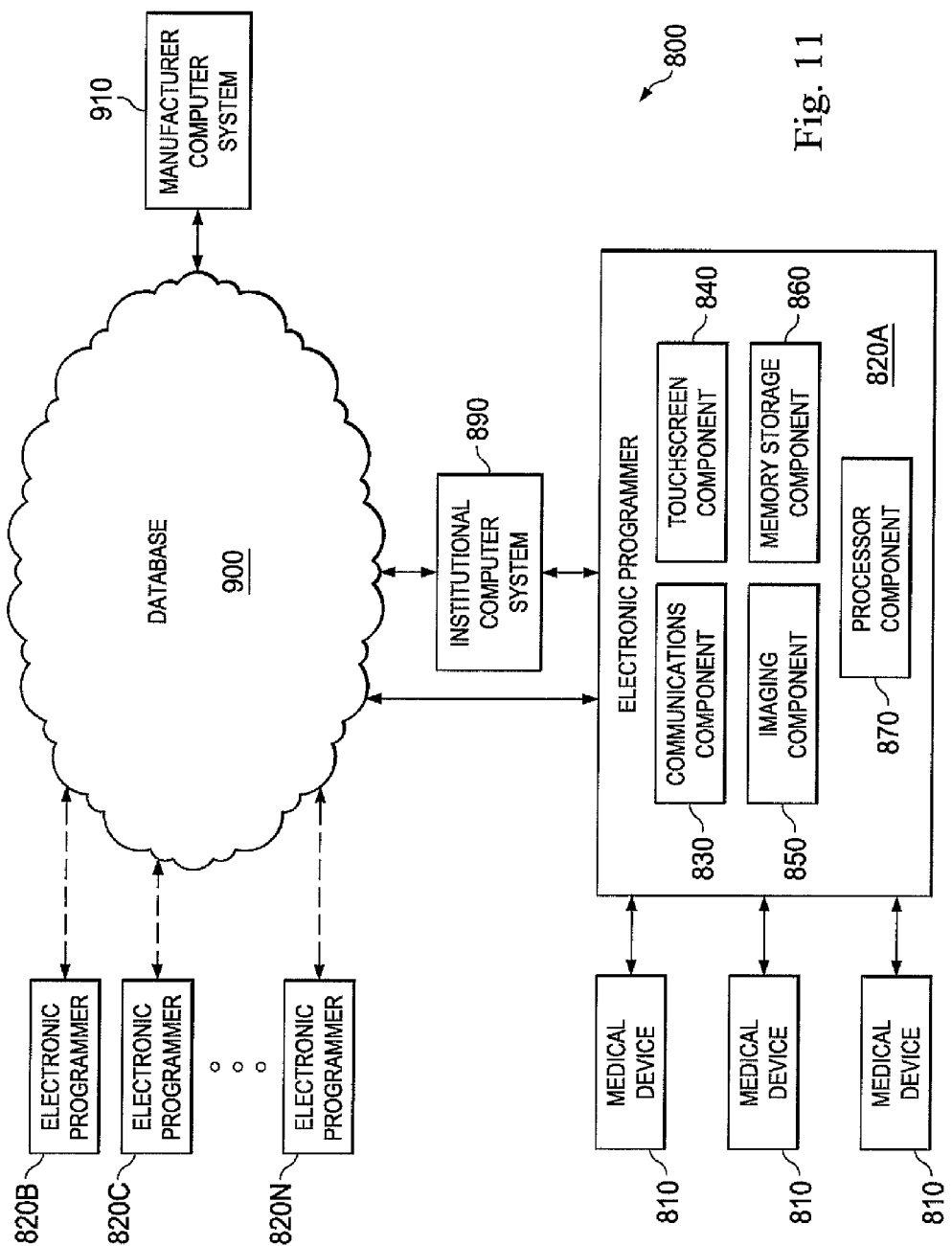
FIG. 11 is a simplified block diagram of a medical system/infrastructure according to various aspects of the present disclosure.

Referring now to FIG. 11, a simplified block diagram of a medical infrastructure 800 (which may also be considered a medical system) is illustrated according to various aspects of the present disclosure. The medical infrastructure 800 includes a plurality of medical devices 810. These medical devices 810 may each be a programmable medical device (or parts thereof) that can deliver a medical therapy to a patient. In some embodiments, the medical devices 810 may include a device of the neurostimulator system discussed above with reference to FIG. 9. For example, the medical devices 810 may be a pulse generator (e.g., the IPG discussed above with reference to FIG. 10), an implantable lead, a charger, or portions thereof. It is understood that each of the medical devices 810 may be a different type of medical device. In other words, the medical devices 810 need not be the same type of medical device.

The medical infrastructure 800 also includes a plurality of electronic programmers 820. For sake of illustration, one of these electronic programmers 820A is illustrated in more detail and discussed in detail below. Nevertheless, it is understood that each of the electronic programmers 820 may be implemented similar to the electronic programmer 820A.

In some embodiments, the electronic programmer 820A may be a clinician programmer, for example the clinician programmer discussed above with reference to FIG. 3. In other embodiments, the electronic programmer 820A may be a patient programmer or another similar programmer. In further embodiments, it is understood that the electronic programmer may be a tablet computer. In any case, the electronic programmer 820A is configured to program the stimulation parameters of the medical devices 810 so that a desired medical therapy can be delivered to a patient.

The electronic programmer 820A contains a communications component 830 that is configured to conduct electronic communications with external devices. For example, the communications device 830 may include a transceiver. The transceiver contains various electronic circuitry components configured to conduct telecommunications with one or more external devices. The electronic circuitry components allow the transceiver to conduct telecommunications in one or more of the wired or wireless telecommunications protocols, including communications protocols such as IEEE 802.11 (Wi-Fi), IEEE 802.15 (Bluetooth), GSM, CDMA, LTE, WIMAX, DLNA, HDMI, Medical Implant Communication Service (MICS), etc. In some embodiments, the transceiver includes antennas, filters, switches, various kinds of amplifiers such as low-noise amplifiers or power amplifiers, digital-to-analog (DAC) converters, analog-to-digital (ADC) converters, mixers, multiplexers and demultiplexers, oscillators, and/or phase-locked loops (PLLs). Some of these electronic circuitry components may be integrated into a single discrete device or an integrated circuit (IC) chip.

The electronic programmer 820A contains a touchscreen component 840. The touchscreen component 840 may display a touch-sensitive graphical user interface that is responsive to gesture-based user interactions. The touch-sensitive graphical user interface may detect a touch or a movement of a user's finger(s) on the touchscreen and interpret these user actions accordingly to perform appropriate tasks. The graphical user interface may also utilize a virtual keyboard to receive user input. In some embodiments, the touch-sensitive screen may be a capacitive touchscreen. In other embodiments, the touch-sensitive screen may be a resistive touchscreen.

It is understood that the electronic programmer 820A may optionally include additional user input/output components that work in conjunction with the touchscreen component 840 to carry out communications with a user. For example, these additional user input/output components may include physical and/or virtual buttons (such as power and volume buttons) on or off the touch-sensitive screen, physical and/or virtual keyboards, mouse, track balls, speakers, microphones, light-sensors, light-emitting diodes (LEDs), communications ports (such as USB or HDMI ports), joy-sticks, etc.

The electronic programmer 820A contains an imaging component 850. The imaging component 850 is configured to capture an image of a target device via a scan. For example, the imaging component 850 may be a camera in some embodiments. The camera may be integrated into the electronic programmer 820A. The camera can be used to take a picture of a medical device, or scan a visual code of the medical device, for example its barcode or Quick Response (QR) code.

The electronic programmer contains a memory storage component 860. The memory storage component 860 may include system memory, (e.g., RAM), static storage 608 (e.g., ROM), or a disk drive (e.g., magnetic or optical), or any other suitable types of computer readable storage media. For example, some common types of computer readable media may include floppy disk, flexible disk, hard disk, magnetic tape, any other magnetic medium, CD-ROM, any other optical medium, RAM, PROM, EPROM, FLASH-EPROM, any other memory chip or cartridge, or any other medium from which a computer is adapted to read. The computer readable medium may include, but is not limited to, non-volatile media and volatile media. The computer readable medium is tangible, concrete, and non-transitory. Logic (for example in the form of computer software code or computer instructions) may be encoded in such computer readable medium. In some embodiments, the memory storage component 860 (or a portion thereof) may be configured as a local database capable of storing electronic records of medical devices and/or their associated patients.

The electronic programmer contains a processor component 870. The processor component 870 may include a central processing unit (CPU), a graphics processing unit (GPU) a microcontroller, a digital signal processor (DSP), or another suitable electronic processor capable of handling and executing instructions. In various embodiments, the processor component 870 may be implemented using various digital circuit blocks (including logic gates such as AND, OR, NAND, NOR, XOR gates, etc.) along with certain software code. In some embodiments, the processor component 870 may execute one or more sequences computer instructions contained in the memory storage component 860 to perform certain tasks.

It is understood that hard-wired circuitry may be used in place of (or in combination with) software instructions to implement various aspects of the present disclosure. Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

It is also understood that the electronic programmer 820A is not necessarily limited to the components 830-870 discussed above, but it may further include additional components that are used to carry out the programming tasks. These additional components are not discussed herein for reasons of simplicity. It is also understood that the medical infrastructure 800 may include a plurality of electronic programmers similar to the electronic programmer 820A discussed herein, but they are not illustrated in FIG. 11 for reasons of simplicity.

The medical infrastructure 800 also includes an institutional computer system 890. The institutional computer system 890 is coupled to the electronic programmer 820A. In some embodiments, the institutional computer system 890 is a computer system of a healthcare institution, for example a hospital. The institutional computer system 890 may include one or more computer servers and/or client terminals that may each include the necessary computer hardware and software for conducting electronic communications and performing programmed tasks. In various embodiments, the institutional computer system 890 may include communications devices (e.g., transceivers), user input/output devices, memory storage devices, and computer processor devices that may share similar properties with the various components 830-870 of the electronic programmer 820A discussed above. For example, the institutional computer system 890 may include computer servers that are capable of electronically communicating with the electronic programmer 820A through the MICS protocol or another suitable networking protocol.

The medical infrastructure 800 includes a database 900. In various embodiments, the database 900 is a remote database—that is, located remotely to the institutional computer system 890 and/or the electronic programmer 820A. The database 900 is electronically or communicatively (for example through the Internet) coupled to the institutional computer system 890 and/or the electronic programmer. In some embodiments, the database 900, the institutional computer system 890, and the electronic programmer 820A are parts of a cloud-based architecture. In that regard, the database 900 may include cloud-based resources such as mass storage computer servers with adequate memory resources to handle requests from a variety of clients. The institutional computer system 890 and the electronic programmer 820A (or their respective users) may both be considered clients of the database 900. In certain embodiments, the functionality between the cloud-based resources and its clients may be divided up in any appropriate manner. For example, the electronic programmer 820A may perform basic input/output interactions with a user, but a majority of the processing and caching may be performed by the cloud-based resources in the database 900. However, other divisions of responsibility are also possible in various embodiments.

According to the various aspects of the present disclosure, electronic data may be uploaded from the electronic programmer 820A to the database 900. The data in the database 900 may thereafter be downloaded by any of the other electronic programmers 820B-820N communicatively coupled to it, assuming the user of these programmers has the right login permissions.

The database 900 may also include a manufacturer's database in some embodiments. It may be configured to manage an electronic medical device inventory, monitor manufacturing of medical devices, control shipping of medical devices, and communicate with existing or potential buyers (such as a healthcare institution). For example, communication with the buyer may include buying and usage history of medical devices and creation of purchase orders. A message can be automatically generated when a client (for example a hospital) is projected to run out of equipment, based on the medical device usage trend analysis done by the database. According to various aspects of the present disclosure, the database 900 is able to provide these functionalities at least in part via communication with the electronic programmer 820A and in response to the data sent by the electronic programmer 820A. These functionalities of the database 900 and its communications with the electronic programmer 820A will be discussed in greater detail later.

The medical infrastructure 800 further includes a manufacturer computer system 910. The manufacturer computer system 910 is also electronically or communicatively (for example through the Internet) coupled to the database 900. Hence, the manufacturer computer system 910 may also be considered a part of the cloud architecture. The computer system 910 is a computer system of medical device manufacturer, for example a manufacturer of the medical devices 810 and/or the electronic programmer 820A.

In various embodiments, the manufacturer computer system 910 may include one or more computer servers and/or client terminals that each includes the necessary computer hardware and software for conducting electronic communications and performing programmed tasks. In various embodiments, the manufacturer computer system 910 may include communications devices (e.g., transceivers), user input/output devices, memory storage devices, and computer processor devices that may share similar properties with the various components 830-870 of the electronic programmer 820A discussed above. Since both the manufacturer computer system 910 and the electronic programmer 820A are coupled to the database 900, the manufacturer computer system 910 and the electronic programmer 820A can conduct electronic communication with each other.

Figure 12:
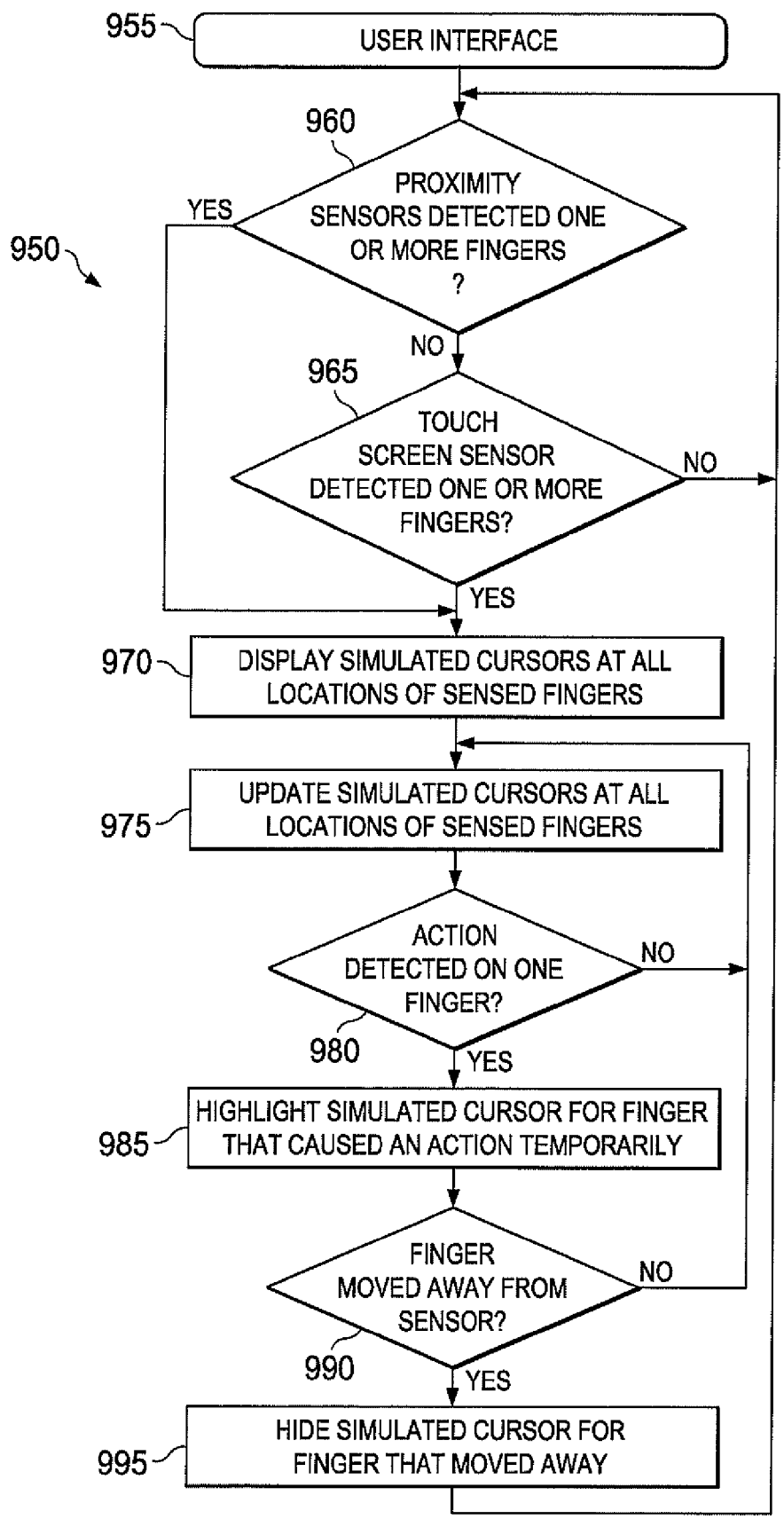
FIGS. 12-13 are simplified flowcharts illustrating a method of visualizing a user interaction with a clinician programmer according to various aspects of the present disclosure.

FIG. 12 is a flowchart 950 illustrating a method of displaying a simulated cursor according to an embodiment of the present disclosure. The method 950 includes a step 955, in which a user interface of a clinician programmer is activated. The method 950 includes a decision step 960 to determine whether the proximity sensors on the clinician programmer have detected one or more fingers. If the answer from the step 960 is yes, then the method 950 proceeds to step 970. If the answer from the step 960 is no, then the method 950 proceeds to a decision step 965 to determine whether the touch screen sensors on the clinician programmer have detected one or more fingers. If the answer from the step 965 is no, the method 950 loops back to the decision step 960. If the answer from the step 965 is yes, the method 950 proceeds to the decision step 970, in which one or more simulated cursors are displayed at all locations of sensed fingers.

The method 950 proceeds to step 975, in which the simulated cursors are updated at all locations of the sensed fingers. The method 950 then proceeds to a decision step 980 to determine whether action is detected on one finger. If the answer from the decision step 980 is no, then the method 950 loops back to the step 975. If the answer from the decision step 980 is yes, then the method 950 proceeds to a step 985 to highlight the simulated cursor for the finger that caused an action temporarily. The method 950 continues to a decision step 990 to determine whether the finger has moved away from the area of the screen corresponding to the simulated cursor. If the answer from the decision step 990 is no, then the method 950 loops back to the step 975. If the answer from the decision step 990 is yes, then the method 950 proceeds to step 995 to hide simulated cursor for the finger that moved away.

It is understood that though the method 950 refers to fingers as an example, other input devices such as styluses may also trigger the display of the simulated cursors in a similar manner. It is also understood that the method 950 may include additional steps that are performed before, during, or after the steps 955-995 discussed herein, but these steps are not specifically discussed for reasons of simplicity. In addition, it is understood that multi-touch functionalities may be implemented for each of the steps 955-995 in some embodiments. Multi-touch may refer to a touch sensitive interface's (such as a touchscreen or a touchpad) capability of detecting the presence of multiple points of contact with the interface. For example, the touch sensitive interface may be able to translate the detection of the engagement (or movement) of one finger with the interface as one command, but may translate the engagement (or movement) of two or three fingers with the interface as a different type of command.

Figure 13:
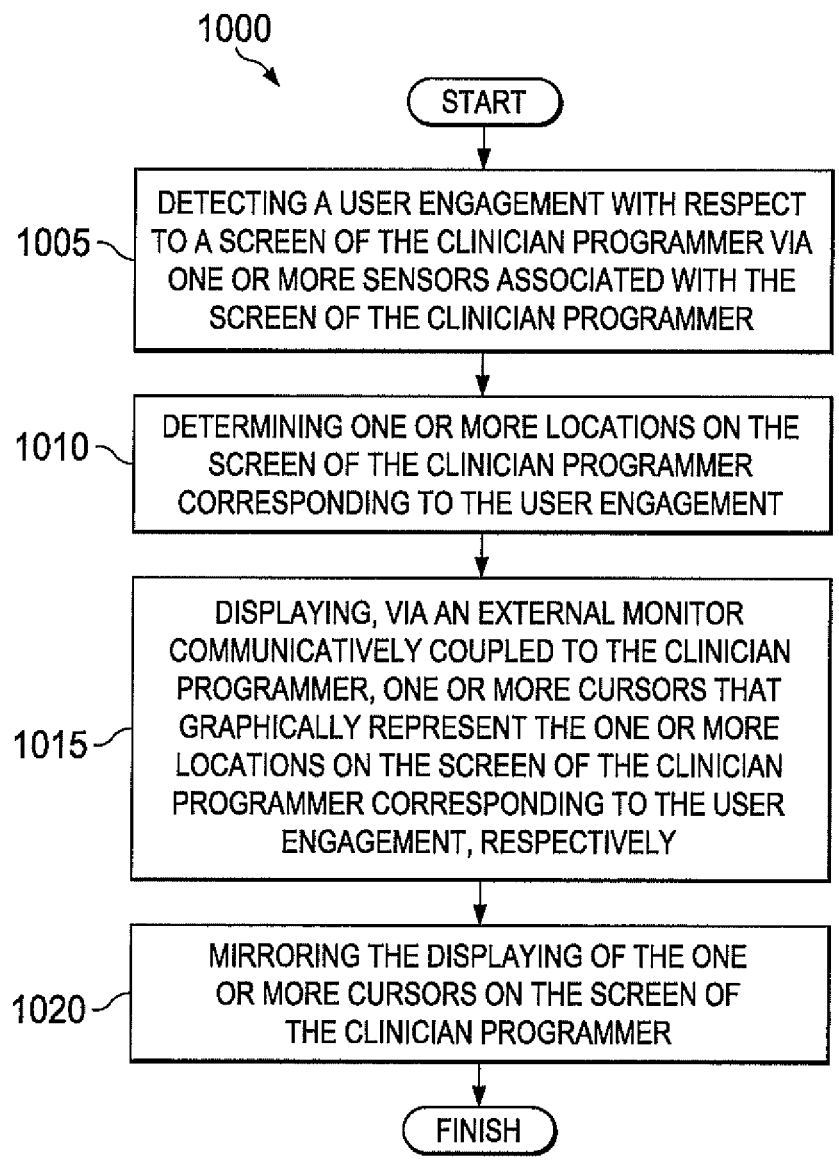

FIG. 13 is a flowchart 1000 illustrating a method of visualizing a user interaction with a clinician programmer according to an embodiment of the present disclosure. The clinician programmer is configured to program a pulse generator so that the pulse generator delivers an electrical stimulation therapy to a patient.

The method 1000 includes a step 1005 of detecting a user engagement with respect to a screen of the clinician programmer via one or more sensors associated with the screen of the clinician programmer. In some embodiments, the step 1005 of detecting includes detecting a physical contact of the screen of the clinician programmer via a touch sensor of the clinician programmer. In some embodiments, a physical contact from a finger or a stylus is detected. In some embodiments, the step 1005 of detecting includes detecting a proximity of a finger or a stylus via a proximity sensor of the clinician programmer. In some embodiments, the engagement from the user invokes an action on the clinician programmer.

The method 1000 includes a step 1010 of determining one or more locations on the screen of the clinician programmer corresponding to the user engagement.

The method 1000 include a step 1015 of displaying, via an external monitor communicatively coupled to the clinician programmer, one or more cursors that graphically represent the one or more locations on the screen of the clinician programmer corresponding to the user engagement, respectively. In some embodiments, the step 1015 of displaying comprises graphically differentiating a selected one of the cursors from the rest of the cursors, wherein the selected one of the cursors corresponds to the invoked action. In some embodiments, the step 1015 of displaying is performed in a manner such that a majority of an area covered by the cursors is transparent. In some embodiments, the external monitor is multiple times larger in size than the clinician programmer. In some embodiments, the external monitor and the clinician programmer are located in separate rooms.

The method 1000 includes a step 1020 of mirroring the displaying of the one or more cursors on the screen of the clinician programmer.

It is also understood that the method 950 may include additional steps that are performed before, during, or after the steps 905-945 discussed herein, but these steps are not specifically discussed for reasons of simplicity.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of visualizing a user interaction with a clinician programmer, the method comprising:
    a) detecting a user engagement with respect to a screen of the clinician programmer via one or more sensors associated with the screen of the clinician programmer;
    b) determining one or more locations on the screen of the clinician programmer corresponding to the user engagement; and
    c) displaying, via an external monitor communicatively coupled to the clinician programmer, one or more cursors that graphically represent the one or more locations on the screen of the clinician programmer corresponding to the user engagement, respectively.

2. The method of claim 1, further comprising mirroring the displaying of the one or more cursors on the screen of the clinician programmer.

3. The method of claim 1, wherein the detecting comprises detecting a physical contact of the screen of the clinician programmer via a touch sensor of the clinician programmer.

4. The method of claim 3, wherein the detecting the physical contact comprises detecting a physical contact from a finger or a stylus.

5. The method of claim 1, wherein the detecting comprises detecting a proximity of a finger or a stylus via a proximity sensor of the clinician programmer.

6. The method of claim 1, wherein the engagement from the user invokes an action on the clinician programmer, and wherein the displaying comprises graphically differentiating a selected one of the cursors from the rest of the cursors, wherein the selected one of the cursors corresponds to the invoked action.

7. The method of claim 1, wherein the displaying is performed in a manner such that a majority of an area covered by the cursors is transparent.

8. The method of claim 1, wherein the external monitor is multiple times larger in size than the clinician programmer.

9. The method of claim 1, wherein the external monitor and the clinician programmer are located in separate rooms.

10. The method of claim 1, wherein the clinician programmer is configured to program a pulse generator so that the pulse generator delivers an electrical stimulation therapy to a patient.

\* \* \* \* \*